US012102384B2

(12) United States Patent
Cook et al.

(10) Patent No.: US 12,102,384 B2
(45) Date of Patent: Oct. 1, 2024

(54) DYNAMIC INTRAVASCULAR LITHOTRIPSY DEVICE WITH MOVABLE ENERGY GUIDE

(71) Applicant: Bolt Medical, Inc., Carlsbad, CA (US)

(72) Inventors: Christopher A. Cook, Laguna Niguel, CA (US); Eric Schultheis, San Clemente, CA (US)

(73) Assignee: Bolt Medical, Inc., Carlsbad, CA (US)

( * ) Notice: Subject to any disclaimer, the term of this patent is extended or adjusted under 35 U.S.C. 154(b) by 254 days.

(21) Appl. No.: 17/094,622

(22) Filed: Nov. 10, 2020

(65) Prior Publication Data
US 2021/0137598 A1     May 13, 2021

Related U.S. Application Data

(60) Provisional application No. 62/934,931, filed on Nov. 13, 2019.

(51) Int. Cl.
*A61B 18/26*     (2006.01)
*A61B 17/00*     (2006.01)
(Continued)

(52) U.S. Cl.
CPC .... *A61B 18/26* (2013.01); *A61B 2017/00154* (2013.01); *A61B 2017/00539* (2013.01);
(Continued)

(58) Field of Classification Search
CPC .......... A61B 18/26; A61B 2017/00154; A61B 2017/00539; A61B 2018/0022;
(Continued)

(56) References Cited

U.S. PATENT DOCUMENTS

| 4,649,924 A | 3/1987 | Taccardi |
| 4,699,147 A | 10/1987 | Chilson et al. |

(Continued)

FOREIGN PATENT DOCUMENTS

| AU | 2017205323 | 1/2022 |
| AU | 2019452180 | 1/2022 |

(Continued)

OTHER PUBLICATIONS

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.

(Continued)

*Primary Examiner* — Carl H Layno
*Assistant Examiner* — Aya Ziad Bakkar
(74) *Attorney, Agent, or Firm* — ROEDER & BRODER LLP; James P. Broder

(57) ABSTRACT

A catheter system for treating a treatment site within or adjacent to a blood vessel within a body of a patient, the treatment site having a proximal region and a distal region, includes an energy source, a guide shaft, and an energy guide. The energy source generates energy. The guide shaft is positionable adjacent to the treatment site. The energy guide receives energy from the energy source. The energy guide is movably coupled to the guide shaft. The energy guide includes a guide distal end that is configured to be positioned adjacent to the treatment site. The guide distal end of the energy guide is selectively movable relative to the guide shaft and adjacent to and between the proximal region and the distal region of the treatment site while the energy guide receives energy from the energy source.

26 Claims, 10 Drawing Sheets

(51) Int. Cl.
*A61B 18/00* (2006.01)
*A61M 25/01* (2006.01)
*A61M 25/06* (2006.01)

(52) U.S. Cl.
CPC .............. *A61B 2018/00196* (2013.01); *A61B 2018/0022* (2013.01); *A61B 2018/266* (2013.01); *A61M 25/0113* (2013.01); *A61M 2025/0681* (2013.01)

(58) Field of Classification Search
CPC ........... A61B 2018/266; A61B 18/245; A61M 25/0113; A61M 2025/0681
See application file for complete search history.

(56) References Cited

U.S. PATENT DOCUMENTS

| | | | |
|---|---|---|---|
| 4,799,479 A | 1/1989 | Spears | |
| 4,850,351 A | 7/1989 | Herman | |
| 4,913,142 A | 4/1990 | Kittrell et al. | |
| 4,932,954 A | 6/1990 | Wondrazek et al. | |
| 4,955,895 A | 9/1990 | Sugiyama | |
| 4,960,108 A | 10/1990 | Reichel et al. | |
| 4,994,059 A | 2/1991 | Kosa et al. | |
| 4,998,930 A | 3/1991 | Lundahl | |
| 5,034,010 A | 7/1991 | Kittrell et al. | |
| 5,041,121 A | 8/1991 | Wondrazek et al. | |
| 5,082,343 A | 1/1992 | Coult et al. | |
| 5,093,877 A | 3/1992 | Aita et al. | |
| 5,104,391 A | 4/1992 | Ingle | |
| 5,104,392 A | 4/1992 | Kittrell et al. | |
| 5,109,452 A | 4/1992 | Selvin et al. | |
| 5,116,227 A | 5/1992 | Levy | |
| 5,126,165 A | 6/1992 | Akiyama et al. | |
| 5,152,768 A | 10/1992 | Bhatta | |
| 5,173,049 A | 12/1992 | Levy | |
| 5,176,674 A | 1/1993 | Hofmann | |
| 5,181,921 A | 1/1993 | Makita et al. | |
| 5,200,838 A | 4/1993 | Nudelman | |
| 5,290,277 A | 3/1994 | Vercimak et al. | |
| 5,324,282 A | 6/1994 | Dodick | |
| 5,372,138 A | 12/1994 | Crowley | |
| 5,387,225 A | 2/1995 | Euteneur | |
| 5,400,428 A | 3/1995 | Grace | |
| 5,422,926 A | 6/1995 | Smith | |
| 5,454,809 A | 10/1995 | Janssen | |
| 5,456,680 A | 10/1995 | Taylor | |
| 5,474,537 A | 12/1995 | Solar | |
| 5,509,917 A | 4/1996 | Cecchetti | |
| 5,540,679 A | 7/1996 | Fram | |
| 5,562,657 A | 10/1996 | Griffin | |
| 5,598,494 A | 1/1997 | Behrmann et al. | |
| 5,609,606 A | 3/1997 | O'Boyle | |
| 5,611,807 A | 3/1997 | O'Boyle | |
| 5,661,829 A | 8/1997 | Zheng | |
| 5,697,377 A | 12/1997 | Wittkamph | |
| 5,718,241 A | 2/1998 | Ben-Haim et al. | |
| 5,729,583 A | 3/1998 | Tang | |
| 5,764,843 A | 6/1998 | Macken et al. | |
| 5,772,609 A | 6/1998 | Nguyen et al. | |
| 5,860,974 A | 1/1999 | Abele | |
| 5,891,135 A | 4/1999 | Jackson et al. | |
| 5,906,611 A | 5/1999 | Dodick et al. | |
| 5,944,697 A | 8/1999 | Benett et al. | |
| 6,015,404 A | 1/2000 | Altshuler | |
| 6,080,119 A | 6/2000 | Schwarze et al. | |
| 6,123,923 A | 9/2000 | Unger | |
| 6,139,510 A | 10/2000 | Palermo | |
| 6,186,963 B1 | 2/2001 | Schwarze et al. | |
| 6,203,537 B1 | 3/2001 | Adrian | |
| 6,210,404 B1 | 4/2001 | Shadduck | |
| 6,339,470 B1 | 1/2002 | Papademetriou et al. | |
| 6,356,575 B1 | 3/2002 | Fukumoto | |
| 6,368,318 B1 | 4/2002 | Visuri et al. | |
| 6,500,174 B1 | 12/2002 | Maguire et al. | |
| 6,514,203 B2 | 2/2003 | Bukshpan | |
| 6,514,249 B1 | 2/2003 | Maguire | |
| 6,524,251 B2 | 3/2003 | Rabiner et al. | |
| 6,538,739 B1 | 3/2003 | Visuri et al. | |
| 6,560,387 B1 | 5/2003 | Hehlen et al. | |
| 6,607,502 B1 | 8/2003 | Maguire et al. | |
| 6,631,220 B1 | 10/2003 | Liang et al. | |
| 6,652,547 B2 | 11/2003 | Rabiner et al. | |
| 6,666,834 B2 | 12/2003 | Restle et al. | |
| 6,773,447 B2 | 8/2004 | Laguna | |
| 6,849,994 B1 | 2/2005 | White et al. | |
| 6,947,785 B1 | 9/2005 | Beatty et al. | |
| 6,966,890 B2 | 11/2005 | Coyle et al. | |
| 6,978,168 B2 | 12/2005 | Beatty et al. | |
| 6,990,370 B1 | 1/2006 | Beatty et al. | |
| 7,309,324 B2 | 12/2007 | Hayes et al. | |
| 7,470,240 B2 | 12/2008 | Schultheiss et al. | |
| 7,539,231 B1 | 5/2009 | Honea et al. | |
| 7,569,032 B2 | 8/2009 | Naimark et al. | |
| 7,599,588 B2 | 10/2009 | Eberle et al. | |
| 7,713,260 B2 | 5/2010 | Lessard | |
| 7,758,572 B2 | 7/2010 | Weber et al. | |
| 7,810,395 B2 | 10/2010 | Zhou | |
| 7,850,685 B2 | 12/2010 | Kunis et al. | |
| 7,867,178 B2 | 1/2011 | Simnacher | |
| 7,972,299 B2 | 7/2011 | Carter | |
| 7,985,189 B1 | 7/2011 | Ogden et al. | |
| 8,162,859 B2 | 4/2012 | Schultheiss et al. | |
| 8,166,825 B2 | 5/2012 | Zhou | |
| 8,192,368 B2 | 6/2012 | Woodruff | |
| 8,292,913 B2 | 10/2012 | Warnack | |
| 8,328,820 B2 | 12/2012 | Diamant | |
| 8,364,235 B2 | 1/2013 | Kordis et al. | |
| 8,419,613 B2 | 4/2013 | Saadat | |
| 8,439,890 B2 | 5/2013 | Beyar | |
| 8,556,813 B2 | 10/2013 | Cashman et al. | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,289,132 B2 | 3/2016 | Ghaffari et al. | |
| 9,289,224 B2 | 3/2016 | Adams et al. | |
| 9,320,530 B2 | 4/2016 | Grace | |
| 9,333,000 B2 | 5/2016 | Hakala et al. | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,730,715 B2 | 8/2017 | Adams | |
| 9,764,142 B2 | 9/2017 | Imran | |
| 9,814,476 B2 | 11/2017 | Adams et al. | |

(56) References Cited

U.S. PATENT DOCUMENTS

| | | |
|---|---|---|
| 9,861,377 B2 | 1/2018 | Mantell et al. |
| 9,867,629 B2 | 1/2018 | Hawkins et al. |
| 9,894,756 B2 | 2/2018 | Weinkam et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy |
| 10,405,923 B2 | 9/2019 | Yu et al. |
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,797,684 B1 | 10/2020 | Benz et al. |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,484,327 B2 | 11/2022 | Anderson et al. |
| 11,633,200 B2 | 4/2023 | Anderson et al. |
| 11,779,363 B2 | 10/2023 | Vo |
| 2001/0016761 A1 | 8/2001 | Rudie |
| 2001/0049464 A1 | 12/2001 | Ganz |
| 2001/0051784 A1 | 12/2001 | Brisken |
| 2002/0045811 A1 | 4/2002 | Kittrell et al. |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0247945 A1 | 10/2009 | Levit |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |

(56) References Cited

U.S. PATENT DOCUMENTS

| | | |
|---|---|---|
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1* | 10/2011 | Hastings ............... A61B 18/24 606/15 |
| 2011/0263921 A1 | 10/2011 | Vrba et al. |
| 2011/0275990 A1 | 11/2011 | Besser et al. |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1* | 9/2012 | Stahmann ............... A61B 5/201 600/483 |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0110003 A1 | 5/2013 | Surti |
| 2013/0116714 A1 | 5/2013 | Adams et al. |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2014/0357997 A1 | 12/2014 | Hartmann |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe |
| 2015/0313732 A1 | 11/2015 | Fulton, III |
| 2015/0342678 A1 | 12/2015 | Deladurantaye et al. |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184570 A1* | 6/2016 | Grace ............... A61M 25/104 604/20 |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1* | 4/2019 | Ramanath ............... A61M 25/1029 |
| 2019/0104933 A1 | 4/2019 | Stern |
| 2019/0117242 A1 | 4/2019 | Lawinger |

(56) References Cited

U.S. PATENT DOCUMENTS

| | | |
|---|---|---|
| 2019/0150960 A1 | 5/2019 | Nguyen et al. |
| 2019/0150961 A1 | 5/2019 | Tozzi |
| 2019/0175111 A1 | 6/2019 | Genereux et al. |
| 2019/0175300 A1 | 6/2019 | Horn et al. |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0321100 A1 | 10/2019 | Masotti et al. |
| 2019/0321101 A1 | 10/2019 | Masotti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0398033 A1 | 12/2020 | McGowan et al. |
| 2020/0405333 A1 | 12/2020 | Massimini et al. |
| 2020/0405391 A1 | 12/2020 | Massimini |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook et al. |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |
| 2023/0310073 A1 | 10/2023 | Adams et al. |
| 2024/0189543 A1 | 6/2024 | Salinas |
| 2024/0216062 A1 | 7/2024 | Cook |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |

(56) References Cited

FOREIGN PATENT DOCUMENTS

| | | |
|---|---|---|
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 2879607 | 2/2019 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| GB | 1082397 | 9/1967 |
| JP | S62275446 A | 11/1987 |
| JP | 2008083273 | 4/2008 |
| JP | 2014123147 | 7/2014 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | 1992008515 A2 | 5/1992 |
| WO | WO9208515 | 5/1992 |
| WO | 9902095 A1 | 1/1999 |
| WO | 9920189 A1 | 4/1999 |
| WO | WO200067648 | 11/2000 |
| WO | WO2000067648 A1 | 11/2000 |
| WO | 2001003599 A1 | 1/2001 |
| WO | WO0103599 | 1/2001 |
| WO | 2006006169 A2 | 1/2006 |
| WO | WO2006006169 | 1/2006 |
| WO | WO2009121017 | 10/2009 |
| WO | WO2009149321 A1 | 12/2009 |
| WO | WO2009152352 A2 | 12/2009 |
| WO | 2010042653 A1 | 4/2010 |
| WO | WO2011094379 | 8/2011 |
| WO | 2011126580 A2 | 10/2011 |
| WO | WO2011126580 A3 | 10/2011 |
| WO | WO2012025833 | 3/2012 |
| WO | WO20120052924 A1 | 4/2012 |
| WO | WO2012058156 | 5/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016014999 | 1/2016 |
| WO | WO2016089683 A1 | 6/2016 |
| WO | WO2016090175 | 6/2016 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 2018175322 A1 | 9/2018 |
| WO | WO2018175322 | 9/2018 |
| WO | WO2018191013 | 10/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | 2021086571 A1 | 5/2021 |
| WO | 2021101766 A1 | 5/2021 |
| WO | WO2021096922 A1 | 5/2021 |
| WO | WO2021101766 | 5/2021 |
| WO | WO2021126762 A1 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

Vogel, A., et al. "Acoustic transient generation by laser-produced cavitation bubbles near solid boundaries", Journal Acoustical Society of America, 1988, pp. 719-731, vol. 84.

Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.

Zheng, W., "Optic Lenses Manufactured on Fiber Ends", 2015, Splicer Engineering AFL, Duncan, SC USA.

Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.

Ali, Ziad A., et al. "Intravascular lithotripsy for treatment of stent underexpansion secondary to severe coronary calcification" 2018, European Society of Cardiology.

Ashok, Praveen C., et al. "Raman spectroscopy bio-sensor for tissue discrimination in surgical robotics—full article", Journal of Biophotonics, 2014, pp. 103-109, vol. 7, No. 1-2.

Ashok, Praveen C., et al. "Raman spectroscopy bio-sensor for tissue discrimination in surgical robotics—proof" Journal of Biophotonics 7, 2014, No. 1-2.

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.

(56) References Cited

OTHER PUBLICATIONS

Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method For Fabricating Artificial Kidney Stones Of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions,Theory, and Implications for aser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
Provisional International Search Report and Written Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.

(56) References Cited

OTHER PUBLICATIONS

Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison Of Manual Vs Automatic Annotation To Identify Abnormal Substrate For Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion, issued by the European Patent Office for PCT/2021/XXX, dated Sep. 30, 2021.
International Search Report and Written Opinion, issued by the EP/ISA, in PCT/US2021/048819, dated Jan. 14, 2022.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones For Research On The Mechinisms Of Stone Breakage In Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Jnstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

(56) References Cited

OTHER PUBLICATIONS

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Feb. 19, 2021 in PCT Application Serial No. PCT/US2020/059960.

Schafter+Kirchhoff, Laser Beam Couplers series 60SMS for coupling into single-mode and polarization-maintaining fiber cables, Schafter+Kirchhoff, pp. 1-5, Germany.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

International Preliminary Report on Patentability dated Sep. 15, 2020 in PCT Application Serial No. PCT/US2019/022009.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing. Oct. 2015. (This reference was cited in a prior Information Disclosure Statement. However, the relevant date was missing. The date has now been added.).

Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).

Meng et al., "Accurate Recovery Of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).

Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).

Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).

International Search Report and Written Opinion dated Nov. 8, 2022 in PCT Application Serial No. PCT US/2022/039678.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

(56) References Cited

OTHER PUBLICATIONS

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Varghese, B., et al. "Influence of absorption induced thermal initiation pathway on irradiance threshold for laser induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European Patent Application No. 18185152, mailed Dec. 13, 2018.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, mailed Jan. 16, 2019.

European Search Report, for European Patent Application No. 18185152.8, mailed Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

International Search Report and Written Opinion, PCT Application Serial No. PCT/US2022/047751 issued Feb. 10, 2023, by the European Patent Office.

International Search Report and Written Opinion dated Aug. 20, 2021 in PCT Application Serial No. PCT/US2021/031130.

AccuCoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023.

International Search Report and Written Opinion issued by the European Patent Office, for Serial No. PCT/US2023/011497, dated Apr. 28, 2023.

International Search Report and Written Opinion issued by the European Patent Office, for Serial No. PCT/US2023/012599, dated May 19, 2023.

PathFinder Digital, "Free Space Optics vs. Fiber Optics", 2023.

International Search Report and Written Opinion, issued in Application Serial No. PCT/US2023/016152, dated Jul. 12, 2023.

(56) References Cited

OTHER PUBLICATIONS

Shen, Yajie et al. "High-peak-power and narrow-linewidth Q-switched Ho: YAG laser in-band pumped at 1931 nm." Applied Physics Express 13.5 (2020): 052006. (Year 2020).

* cited by examiner

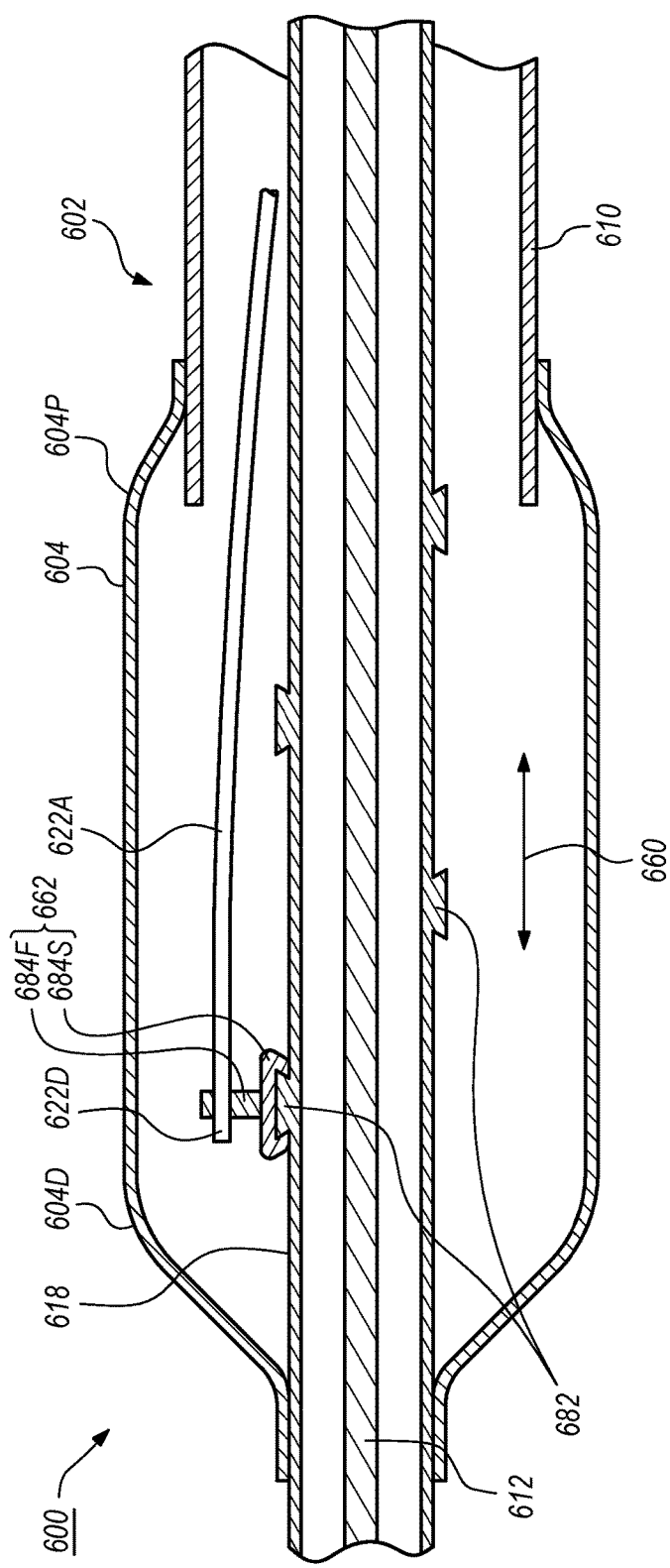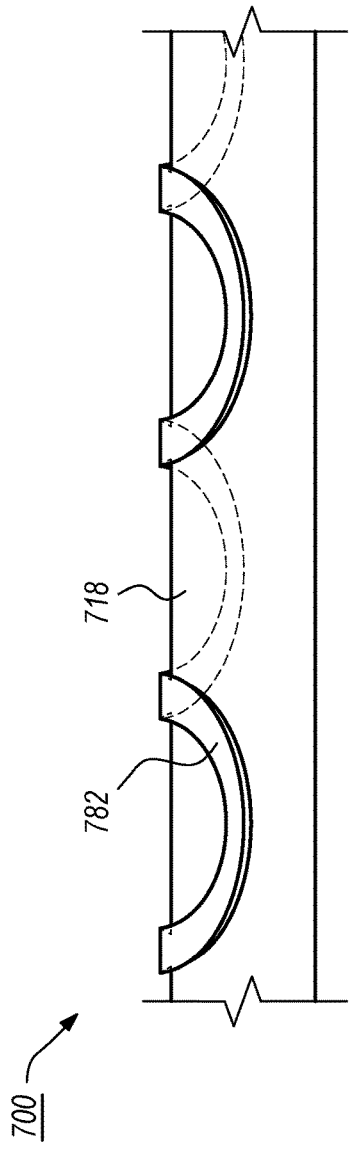

DYNAMIC INTRAVASCULAR LITHOTRIPSY DEVICE WITH MOVABLE ENERGY GUIDE

RELATED APPLICATION

This application claims priority on U.S. Provisional Application Ser. No. 62/934,931, filed on Nov. 13, 2019, and entitled "DYNAMIC LASER-DRIVEN LITHOPLASTY DEVICE AND METHOD". As far as permitted, the contents of U.S. Provisional Application Ser. No. 62/934,931 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Lithoplasty is one method that has been recently used with some success for breaking up vascular lesions within vessels in the body. Lithoplasty utilizes a combination of pressure waves and bubble dynamics that are generated intravascularly in a fluid-filled balloon catheter. In particular, during a lithoplasty treatment, a high energy source is used to generate plasma and ultimately pressure waves as well as a rapid bubble expansion within a fluid-filled balloon to crack calcification at a treatment site within the vasculature that includes one or more vascular lesions. The associated rapid bubble formation from the plasma initiation and resulting localized fluid velocity within the balloon transfers mechanical energy through the incompressible fluid to impart a fracture force on the intravascular calcium, which is opposed to the balloon wall. The rapid change in fluid momentum upon hitting the balloon wall is known as hydraulic shock, or water hammer.

There is an ongoing desire to enhance vessel patency and optimization of therapy delivery parameters within a lithoplasty catheter system.

SUMMARY

The present invention is directed toward a catheter system for treating a treatment site within or adjacent to a blood vessel within a body of a patient. The treatment site has a proximal region and a distal region. In various embodiments, the catheter system includes an energy source, a guide shaft, and an energy guide. The energy source generates energy. The guide shaft is positionable adjacent to the treatment site. The energy guide receives energy from the energy source. The energy guide is movably coupled to the guide shaft. The energy guide includes a guide distal end that is configured to be positioned adjacent to the treatment site. The guide distal end of the energy guide is selectively movable relative to the guide shaft and adjacent to and between the proximal region and the distal region of the treatment site while the energy guide receives energy from the energy source.

In some embodiments, the catheter system can also include an energy guide mover that selectively moves the energy guide so that the guide distal end of the energy guide moves adjacent to and between the proximal region and the distal region of the treatment site while the energy guide receives energy from the energy source.

In certain embodiments, the energy guide mover can include one or more motorized rollers that each engages the energy guide. The one or more motorized rollers selectively move the energy guide adjacent to and between the proximal region and the distal region of the treatment site while the energy guide receives energy from the energy source.

In some embodiments, the energy guide is configured to be manually moved by an operator of the catheter system so that the guide distal end of the energy guide moves adjacent to and between the proximal region and the distal region of the treatment site while the energy guide receives energy from the energy source.

In certain embodiments, the guide shaft includes a guide channel that guides movement of the energy guide relative to the guide shaft. In some such embodiments, the guide channel has a somewhat spiral configuration along a length of the guide shaft. In such embodiments, the guide distal end of the energy guide moves in a substantially spiral manner while the guide distal end moves adjacent to and between the proximal region and the distal region of the treatment site. Alternatively, in other such embodiments, the guide channel has a somewhat sinusoidal configuration along a length of the guide shaft. In such other embodiments, the guide distal end of the energy guide moves in a substantially sinusoidal manner while the guide distal end moves adjacent to and between the proximal region and the distal region of the treatment site.

In some embodiments, the catheter system further includes a catheter shaft that is configured to be selectively positioned near the treatment site. The guide shaft is positioned at least partially within the catheter shaft.

In certain such embodiments, the catheter system can further include an inflatable balloon that is coupled to the catheter shaft, the inflatable balloon including a balloon wall that defines a balloon interior, the inflatable balloon being configured to retain a balloon fluid within the balloon interior. The guide distal end is positioned within the balloon interior and is movable relative to the balloon while the energy guide receives energy from the energy source. In some embodiments, the inflatable balloon is selectively inflatable with the balloon fluid to expand to an inflated state, wherein when the inflatable balloon is in the inflated state the balloon wall is configured to be positioned substantially adjacent to the treatment site.

In some embodiments, the energy source is a light source that is configured to provide sub-millisecond pulses of light energy to the energy guide so that plasma formation is initiated within the inflatable balloon, causing rapid bubble formation that imparts pressure waves upon the treatment site.

In certain embodiments, the energy guide includes an optical fiber that is configured to guide light energy from the light source from a guide proximal end to the guide distal end.

In some embodiments, the energy guide includes a photoacoustic transducer that converts the light energy into an acoustic wave near the distal end of the energy guide.

In certain embodiments, the energy guide includes a diverting feature that directs energy toward a side surface of the guide distal end of the energy guide.

The present invention is also directed toward a method for treating a treatment site within or adjacent to a blood vessel within a body of a patient, the method including the steps of generating energy with an energy source; positioning a guide shaft adjacent to the treatment site; movably coupling an energy guide to the guide shaft, the energy guide including a guide distal end; receiving energy from the energy source with the energy guide; and moving the guide distal end of the energy guide relative to the guide shaft and adjacent to and between a proximal region and a distal region of the treatment site while the energy guide is receiving energy from the energy source.

Additionally, the present invention is further directed toward a catheter system for treating a treatment site within or adjacent to a blood vessel within a body of a patient, the treatment site having a proximal region and a distal region, the catheter system including (i) a light source that generates sub-millisecond pulses of light energy; (ii) a guide shaft that is positionable adjacent to the treatment site, the guide shaft including a guide channel; (iii) a catheter shaft that is configured to be selectively positioned near the treatment site, the guide shaft being positioned at least partially within the catheter shaft; (iv) an inflatable balloon that is coupled to the catheter shaft, the inflatable balloon including a balloon wall that defines a balloon interior, the inflatable balloon being configured to retain a balloon fluid within the balloon interior; (v) an energy guide that receives the light energy from the light source, the energy guide being movably coupled to the guide shaft, the energy guide including a guide distal end that is configured to be positioned adjacent to the treatment site, the energy guide being configured to guide the light energy from the light source from a guide proximal end to a guide distal end so that plasma formation is initiated within the inflatable balloon, causing rapid bubble formation that imparts pressure waves upon the treatment site; and (vi) an energy guide mover that selectively moves the energy guide so that the guide distal end of the energy guide moves adjacent to and between the proximal region and the distal region of the treatment site while the energy guide receives energy from the energy source, the guide channel guiding movement of the energy guide relative to the guide shaft.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6 is a schematic cross-sectional view of a portion of yet another embodiment of the catheter system;

FIG. 7 is a schematic side view of a portion of another embodiment of the catheter system;

Figure 1:
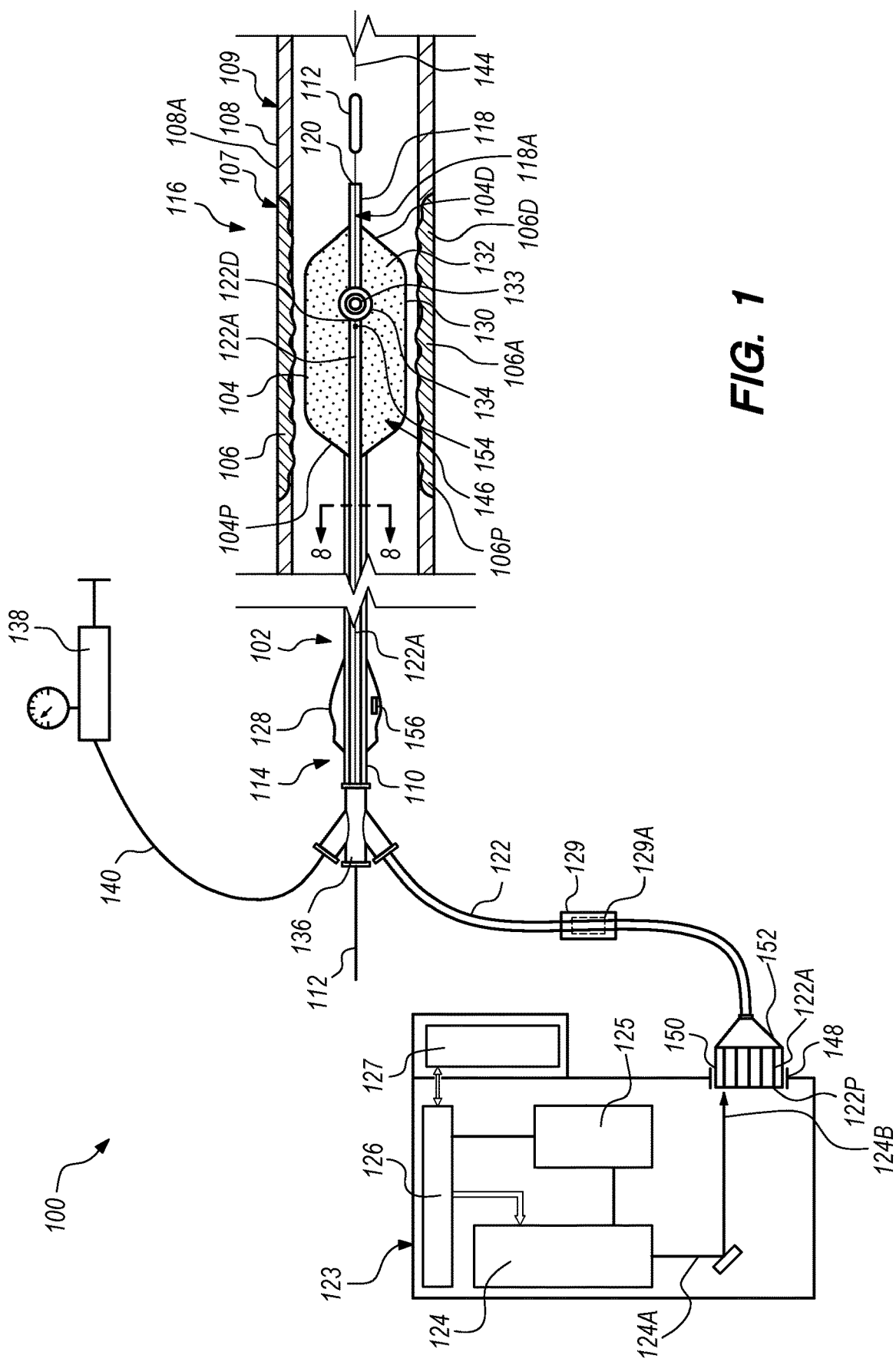
FIG. 1 is a schematic cross-sectional view of an embodiment of a catheter system in accordance with various embodiments.

While embodiments of the present invention are susceptible to various modifications and alternative forms, specifics thereof have been shown by way of example and drawings, and will be described in detail. It is understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

In various embodiments, the catheter systems and related methods disclosed herein can include a catheter configured to advance to a vascular lesion, such as a calcified vascular lesion or a fibrous vascular lesion, at a treatment site located within or adjacent a blood vessel within a body of a patient. The catheter includes a catheter shaft, and an inflatable balloon that is coupled and/or secured to the catheter shaft. The balloon can include a balloon wall that defines a balloon interior. The balloon can be configured to receive a balloon fluid within the balloon interior to expand from a deflated state suitable for advancing the catheter through a patient's vasculature, to an inflated state suitable for anchoring the catheter in position relative to the treatment site.

In certain embodiments, the catheter systems and related methods utilize an energy source, e.g., a light source such as a laser source or another suitable energy source, which provides energy that is guided by one or more energy guides, e.g., light guides such as optical fibers, which are disposed along the catheter shaft and within the balloon interior of the balloon to create a localized plasma in the balloon fluid that is retained within the balloon interior of the balloon. As such, the energy guide can sometimes be referred to as, or can be said to incorporate a "plasma generator" at or near a guide distal end of the energy guide that is positioned within the balloon interior of the balloon located at the treatment site. The creation of the localized plasma can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid retained within the balloon interior of the balloon and thereby impart pressure waves onto and induce fractures in the vascular lesions at the treatment site within or adjacent to the blood vessel wall within the body of the patient. In some embodiments, the energy source can be configured to provide sub-millisecond pulses of energy, e.g., light energy, to initiate the plasma formation in the balloon fluid within the balloon to cause the rapid bubble formation and to impart the pressure waves upon the balloon wall at the treatment site. Thus, the pressure waves can transfer mechanical energy through an incompressible balloon fluid to the treatment site to impart a fracture force on the intravascular lesion. Without wishing to be bound by any particular theory, it is believed that the rapid change in balloon fluid momentum upon the balloon wall that is in contact with the intravascular lesion is transferred to the intravascular lesion to induce fractures to the lesion.

Importantly, in various embodiments, the guide distal end of the energy guide is configured to be positioned near and/or adjacent to the treatment site. More particularly, in such embodiments, the guide distal end of the energy guide is selectively movable adjacent to and between a proximal region and a distal region of the treatment site. In certain such embodiments, the catheter systems and related methods further include an energy guide mover that selectively moves the energy guide so that the guide distal end of the energy guide moves adjacent to and between the proximal region and the distal region of the treatment site while the energy guide receives energy from the energy source. Additionally, or in the alternative, the energy guide can be selectively moved manually by an operator so that the guide distal end of the energy guide moves adjacent to and between the proximal region and the distal region of the treatment site while the energy guide receives energy from the energy source.

As utilized herein, the guide distal end of the energy guide being positioned near and/or adjacent to the treatment site signifies that the guide distal end of the energy guide is at the same approximate longitudinal position relative to a length of the balloon and/or the catheter shaft as is the treatment site.

Additionally, in some embodiments, the energy guides can include one or more diverting features configured to direct energy to exit from the energy guide toward a side surface of the energy guide and toward the balloon wall. In such embodiments, the diverting features direct energy to exit in a direction away from the axis of the energy guide, or in an off-axis direction.

As used herein, the terms "intravascular lesion" and "vascular lesion" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is recognized that such a development effort might be complex and time-consuming, but would nevertheless be a routine undertaking of engineering for those of ordinary skill in the art having the benefit of this disclosure.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more vascular lesions within or adjacent a vessel wall of a blood vessel. In the embodiment illustrated in FIG. 1, the catheter system 100 can include one or more of a catheter 102, an energy guide bundle 122 including one or more energy guides 122A, a source manifold 136, a fluid pump 138, a system console 123 including one or more of an energy source 124, a power source 125, a system controller 126, and a graphic user interface 127 (a "GUI"), a handle assembly 128, and an energy guide mover 129. Alternatively, the catheter system 100 can have more components or fewer components than those specifically illustrated and described in relation to FIG. 1.

The catheter 102 is configured to move to a treatment site 106 within or adjacent to a vessel wall 108A of a blood vessel 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions. As shown, the treatment site 106 can further be said to include a proximal region 106P and a distal region 106D.

The catheter 102 can include an inflatable balloon 104 (sometimes referred to herein simply as a "balloon"), a catheter shaft 110, a guide shaft 118, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The guide shaft 118 is positioned at least partially within the catheter shaft 110. The guide shaft 118 is selectively positionable near and/or adjacent to the treatment site 106. The guide shaft 118 includes and/or defines a guidewire lumen 118A which is configured to move over the guidewire 112. In particular, the guidewire lumen 118A defines a conduit through which the guidewire 112 extends. The catheter shaft 110 can further include an inflation lumen (not shown) and/or various other lumens for various other purposes. In some embodiments, the catheter 102 can have a distal end opening 120 and can accommodate and be tracked over the guidewire 112 as the catheter 102 is moved and positioned at or near the treatment site 106.

As utilized herein, the guide shaft 118 being positioned near and/or adjacent to the treatment site 106 signifies that at least a portion of the guide shaft 118 is at the same approximate longitudinal position relative to a length of the balloon 104 and/or the catheter shaft 110 as is the treatment site 106.

The balloon 104 includes a balloon wall 130 that defines a balloon interior 146. The balloon 104 can be selectively inflated with a balloon fluid 132 to expand from a deflated state suitable for advancing the catheter 102 through a patient's vasculature, to an inflated state (as shown in FIG. 1) suitable for anchoring the catheter 102 in position relative to the treatment site 106. Stated in another manner, when the balloon 104 is in the inflated state, the balloon wall 130 of the balloon 104 is configured to be positioned substantially adjacent to the treatment site 106. It is appreciated that although FIG. 1 illustrates the balloon wall 130 of the balloon 104 being shown spaced apart from the treatment site 106 of the blood vessel 108 when in the inflated state, this is done for ease of illustration. It is recognized that the balloon wall 130 of the balloon 104 will typically be substantially directly adjacent to and/or abutting the treatment site 106 when the balloon 104 is in the inflated state.

The balloon 104 suitable for use in the catheter system 100 includes those that can be passed through the vasculature of a patient when in the deflated state. In some embodiments, the balloons 104 are made from silicone. In other embodiments, the balloon 104 can be made from materials such as polydimethylsiloxane (PDMS), polyurethane, polymers such as PEBAX™ material, nylon, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloon 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The balloon 104 can have various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloon 104 can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluid 132 suitable for use herein is biocompatible. A volume of balloon fluid 132 can be tailored by the chosen light source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as perfluorocarbon dodecafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluid 132 can include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG—emission maximum=1064 nm) lasers, holmium: YAG (Ho:YAG—emission maximum=2.1 μm) lasers, or erbium:YAG (Er:YAG—emission maximum=2.94 μm) lasers. In some embodiments, the absorptive agents can be water soluble. In other embodiments, the absorptive agents are not water soluble. In some embodiments, the absorptive agents used in the balloon fluids 132 can be tailored to match the peak emission of the energy source 124. Various energy sources 124 having emission wavelengths of at least ten nanometers to one millimeter are discussed elsewhere herein.

In some embodiments, introduction of the balloon fluid 132 causes the expansion of the balloon 104 from the deflated state to a first inflated state, and from the first inflated state to a second further inflated state. In addition, or alternatively, the expansion of the balloon 104 can be accomplished using a shape-memory material or other means.

The catheter shaft 110 of the catheter 102 can be coupled to the one or more energy guides 122A of the energy guide bundle 122 that are in optical communication with the energy source 124. The energy guide(s) 122A can be disposed along the catheter shaft 110 and within the balloon 104. In some embodiments, each energy guide 122A can be an optical fiber and the energy source 124 can be a laser. The energy source 124 can be in optical communication with the energy guides 122A at the proximal portion 114 of the catheter system 100.

In some embodiments, the catheter shaft 110 can be coupled to multiple energy guides 122A such as a first energy guide, a second energy guide, a third energy guide, etc., which can be disposed at any suitable positions about the guide shaft 118 and/or the catheter shaft 110. For example, in certain non-exclusive embodiments, two energy guides 122A can be spaced apart by approximately 180 degrees about the circumference of the guide shaft 118 and/or the catheter shaft 110 (see, for example, FIG. 8); three energy guides 122A can be spaced apart by approximately 120 degrees about the circumference of the guide shaft 118 and/or the catheter shaft 110 (see, for example, FIG. 9); four energy guides 122A can be spaced apart by approximately 90 degrees about the circumference of the guide shaft 118 and/or the catheter shaft 110 (see, for example, FIG. 10); five energy guides 122A can be spaced apart by approximately 72 degrees about the circumference of the guide shaft 118 and/or the catheter shaft 110; or six energy guides 122A can be spaced apart by approximately 60 degrees about the circumference of the guide shaft 118 and/or the catheter shaft 110 (see, for example, FIG. 11). Still alternatively, multiple energy guides 122A need not be uniformly spaced apart from one another about the circumference of the guide shaft 118 and/or the catheter shaft 110. More particularly, it is further appreciated that the energy guides 122A can be disposed uniformly or non-uniformly about the guide shaft 118 and/or the catheter shaft 110 to achieve the desired effect in the desired locations.

The catheter system 100 and/or the energy guide bundle 122 can include any number of energy guides 122A in optical communication with the energy source 124 at the proximal portion 114, and with the balloon fluid 132 within the balloon interior 146 of the balloon 104 at the distal portion 116. For example, in some embodiments, the catheter system 100 and/or the energy guide bundle 122 can include from one energy guide 122A to greater than 30 energy guides 122A.

The energy guides 122A can have any suitable design for purposes of generating plasma and/or pressure waves in the balloon fluid 132 within the balloon interior 146. Thus, the general description of the energy guides 122A as light guides is not intended to be limiting in any manner, except for as set forth in the claims appended hereto. More particularly, although the catheter systems 100 are often described with the energy source 124 as a light source and the one or more energy guides 122A as light guides, the catheter system 100 can alternatively include any suitable energy source 124 and energy guides 122A for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, generates the plasma and forms the pressure waves within the balloon fluid 132 that are utilized to provide the fracture force onto the vascular lesions 106A at the treatment site 106. Still alternatively, the energy source 124 and/or the energy guides 122A can have another suitable design and/or configuration.

In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide energy along its length from a guide proximal end 122P to the guide distal end 122D having at least one optical window (not shown) that is positioned within the balloon interior 146.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be disposed spirally or helically about the longitudinal axis 144 of the catheter shaft 110 and/or the guide shaft 118. In some embodiments, the energy guides 122A can be physically coupled to the catheter shaft 110 and/or the guide shaft 118. In other embodiments, the energy guides 122A can be disposed along a length of an outer diameter of the catheter shaft 110 and/or the guide shaft 118. In yet other embodiments, the energy guides 122A can be disposed within one or more energy guide lumens within the catheter shaft 110.

The energy guides 122A can also be disposed at any suitable positions about the circumference of the guide shaft 118 and/or the catheter shaft 110, and the guide distal end 122D of each of the energy guides 122A can be disposed at any suitable longitudinal position relative to the length of the balloon 104 and/or relative to the length of the guide shaft 118. During use, the energy guide 122A will be positioned such that the guide distal end 122D is positioned near and/or adjacent to the treatment site 106. As utilized herein, the guide distal end 122D of the energy guide 122A being positioned near and/or adjacent to the treatment site 106 signifies that the guide distal end 122D of the energy guide 122A is at the same approximate longitudinal position relative to a length of the balloon 104, the catheter shaft and/or the guide shaft 118 as is the treatment site 106.

Certain non-exclusive alternative embodiments for the positioning of the energy guides 122A relative to the guide shaft 118 and/or the catheter shaft 110 are illustrated in FIGS. 7-11.

In certain embodiments, the energy guides 122A can include one or more photoacoustic transducers 154, where each photoacoustic transducer 154 can be in optical communication with the energy guide 122A within which it is disposed. It is appreciated that each energy guide 122A can include any suitable number of photoacoustic transducers 154. For example, in some such embodiments, the energy guide 122A can include anywhere from one photoacoustic transducer 154 to greater than 40 photoacoustic transducers 154. In embodiments that include more than one photoacoustic transducer 154, the photoacoustic transducers 154 can be positioned anywhere along a length of the energy guide 122A. Additionally, in such embodiments, the photoacoustic transducers 154 can be positioned in any suitable relationship to one another radially about the energy guide 122A. For example, the photoacoustic transducers 154 can be spaced apart radially about the energy guide 122A by approximately 1 degree, 2 degrees, 5 degrees, 10 degrees, 20 degrees, 30 degrees, 45 degrees, 60 degrees, 90 degrees, 180 degrees, or another suitable amount.

In some embodiments, the photoacoustic transducers 154 can be in optical communication with the guide distal end 122D of the energy guide 122A. Additionally, in such embodiments, the photoacoustic transducers 154 can have a shape that corresponds with and/or conforms to the guide distal end 122D of the energy guide 122A. In particular, in certain embodiments, the photoacoustic transducers 154 disposed at the guide distal end 122D of the energy guide 122A can assume the same shape as the guide distal end 122D of the energy guide 122A. For example, in certain non-exclusive embodiments, the photoacoustic transducer 154 and/or the guide distal end 122D can have a cylindrical shape, an angled shape, a tapered shape, a conical shape, a convex shape, a concave shape, a bulbous shape, a square shape, a stepped shape, a half-circle shape, an ovoid shape, and the like. The energy guide 122A can further include additional photoacoustic transducers 154 disposed along one or more side surfaces of the length of the energy guide 122A.

The photoacoustic transducer 154 is configured to convert light energy into an acoustic wave at or near the guide distal end 122D of the energy guide 122A. The direction of the acoustic wave can be tailored by changing an angle of the guide distal end 122D of the energy guide 122A.

In some embodiments, each energy guide 122A can further include one or more diverting features or "diverters" (not shown in FIG. 1) within the energy guide 122A that are configured to direct energy to exit the energy guide 122A toward a side surface which can be located at or near the guide distal end 122D of the energy guide 122A, and toward the balloon wall 130. A diverting feature can include any feature of the system that diverts energy from the energy guide 122A away from its axial path toward a side surface of the energy guide 122A. Additionally, the energy guides 122A can each include one or more optical windows disposed along the longitudinal or circumferential surfaces of each energy guide 122A and in optical communication with a diverting feature. Stated in another manner, the diverting features can be configured to direct energy in the energy guide 122A toward a side surface that is at or near the guide distal end 122D, where the side surface is in optical communication with an optical window. The optical windows can include a portion of the energy guide 122A that allows energy to exit the energy guide 122A from within the energy guide 122A, such as a portion of the energy guide 122A lacking a cladding material on or about the energy guide 122A. It is appreciated that each energy guide 122A can include any suitable number of diverting features and any suitable number of optical windows.

Examples of the diverting features suitable for use include a reflecting element, a refracting element, and a fiber diffuser. The diverting features suitable for focusing energy away from the tip of the energy guides 122A can include, but are not to be limited to, those having a convex surface, a gradient-index (GRIN) lens, and a mirror focus lens. Additionally, the diverting features can be formed from any suitable materials, such as a glass, a polymer, a mirror, a reflective metal coating, or another suitable material. Upon contact with the diverting feature, the energy is diverted within the energy guide 122A to one or more of a plasma generator 133 and the photoacoustic transducer 154 that is in optical communication with a side surface of the energy guide 122A. The photoacoustic transducer 154 then converts light energy into an acoustic wave that extends away from the side surface of the energy guide 122A.

Certain non-exclusive alternative embodiments of the guide distal end 122D of the energy guide 122A including one or more photoacoustic transducers 154 and/or one or more diverting features are illustrated and described in relation to FIGS. 12-15.

The source manifold 136 can be positioned at or near the proximal portion 114 of the catheter system 100. The source manifold 136 can include one or more proximal end openings that can receive the one or more energy guides 122A of the energy guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided within the catheter system 100 without the specific need for the system console 123.

As shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a "socket") by which the energy guide bundle 122 is mechanically coupled to the system console 123. In such embodiments, the energy guide bundle 122 can include a guide coupling housing 150 (also sometimes referred to generally as a "ferrule") that houses a portion, e.g., the guide proximal end 122P, of each of the energy guides 122A. The guide coupling housing 150 is configured to fit and be selectively retained within the console connection aperture 148 to provide the mechanical coupling between the energy guide bundle 122 and the system console 123.

The energy guide bundle 122 can also include a guide bundler 152 (or "shell") that brings each of the individual energy guides 122A closer together so that the energy guides 122A and/or the energy guide bundle 122 can be in a more compact form as it extends with the catheter 102 into the blood vessel 108 during use of the catheter system 100.

The energy source 124 can be selectively and/or alternatively coupled in optical communication with each of the energy guides 122A, i.e. to the guide proximal end 122P of each of the energy guides 122A, in the energy guide bundle 122. In particular, the energy source 124 is configured to generate energy in the form of a source beam 124A, such as a pulsed source beam, that can be selectively and/or alternatively directed to and received by each of the energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, the energy source 124 can be configured to provide sub-millisecond pulses of energy from the energy source 124 that are focused onto a small spot in order to couple it into the guide proximal end 122P of the energy guide 122A. Such pulses of energy are then directed and/or guided along the energy guides 122A to a location within the balloon interior 146 of the balloon 104, thereby inducing plasma formation in the balloon fluid 132 within the balloon interior 146 of the balloon 104, e.g., via the plasma generator 133 that can be located at the guide distal end 122D of the energy guide 122A. In particular, the energy emitted at the guide distal end 122D of the energy guide 122A energizes the plasma generator 133 to form the plasma within the balloon fluid 132 within the balloon interior 146. The plasma formation causes rapid bubble formation, and imparts pressure waves upon the treatment site 106. An exemplary plasma-induced bubble 134 is illustrated in FIG. 1.

In various non-exclusive alternative embodiments, the sub-millisecond pulses of energy from the energy source 124 can be delivered to the treatment site 106 at a frequency of between approximately one hertz (Hz) and 5000 Hz, approximately 30 Hz and 1000 Hz, approximately ten Hz and 100 Hz, or approximately one Hz and 30 Hz. Alternatively, the sub-millisecond pulses of energy can be delivered to the treatment site 106 at a frequency that can be greater than 5000 Hz or less than one Hz, or any other suitable range of frequencies.

It is appreciated that although the energy source 124 is typically utilized to provide pulses of energy, the energy source 124 can still be described as providing a single source beam 124A, i.e. a single pulsed source beam.

The energy sources 124 suitable for use can include various types of light sources including lasers and lamps. Alternatively, the energy sources 124 can include any suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter systems 100 can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter systems 100 can generate pressure waves having maximum pressures in the range of at least approximately two MPa to 50 MPa, at least approximately two MPa to 30 MPa, or approximately at least 15 MPa to 25 MPa.

Therapeutic treatment can act via a fatigue mechanism or a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa. Pressures between the extreme ends of these two ranges may act upon a treatment site using a combination of a fatigue mechanism and a brute force mechanism.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the energy source 124, the system controller 126, the GUI 127, the handle assembly 128, and the energy guide mover 129. The power source 125 can have any suitable design for such purposes. For example, in certain non-exclusive alternative embodiments, the power source 125 can be configured to provide one or more of hydraulic power, pneumatic power, electric power, magnetic power, thermal power, mechanical power, and electromechanical power to each of the energy source 124, the system controller 126, the GUI 127, the handle assembly 128, and the energy guide mover 129. Stated in another manner, in such embodiments, each of the energy source 124, the system controller 126, the GUI 127, the handle assembly 128, and the energy guide mover 129 can be one or more of hydraulically powered, pneumatically powered, electrically powered, magnetically powered, thermally powered, mechanically powered, and electromechanically powered.

The system controller 126 is electrically coupled to and receives power from the power source 125. Additionally, the system controller 126 is coupled to and is configured to control operation of each of the energy source 124 and the GUI 127. The system controller 126 can include one or more processors or circuits for purposes of controlling the operation of at least the energy source 124 and the GUI 127. For example, the system controller 126 can control the energy source 124 for generating pulses of energy as desired and/or at any desired firing rate.

The system controller 126 can also be configured to control operation of other components of the catheter system 100 such as the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, and the GUI 127. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

In various implementations, the energy guide mover 129 can move the energy guide(s) 122A proximally and/or distally relative to the catheter shaft 110, the balloon 104, the guide shaft 118, and/or the treatment site 106 (i.e. the vascular lesions 106A at the treatment site 106). For example, in some such implementations, the energy guide mover 129 is usable to move the energy guide(s) 122A so that the guide distal end 122D is moved between the balloon proximal end 104P and the balloon distal end 104D. Additionally, or in the alternative, in other such implementations, the energy guide mover 129 is usable to move the energy guide(s) 122A so that the guide distal end 122D is moved adjacent to and/or between the proximal region 106P and the distal region 106D of the treatment site 106. It is appreciated that the catheter shaft 110, the balloon 104 and the guide shaft 118 can be substantially stationary during the movement of the energy guide 122A and/or the guide distal end 122D adjacent to and/or between the proximal region 106P and the distal region 106D of the treatment site 106.

In one embodiment, the energy guide mover 129 can include a drive mechanism or other actuator, such as one or more motorized rollers 129A (illustrated as a box in phantom). In alternative embodiments, the energy guide mover 129 can include other motors, or any other suitable type of drive mechanism that can move the energy guide(s) 122A proximally and/or distally relative to the catheter shaft 110, the balloon 104 and/or the guide shaft 118. Further, as provided in greater detail herein, the positioning of the energy guide mover 129 can be varied. In the embodiment illustrated in FIG. 1, the energy guide mover 129 can be positioned outside, e.g., proximal to, the catheter shaft 110. As used in this context, "proximal" is intended to mean toward the energy source 124, and/or between the energy source 124 and the catheter shaft 110. In another embodiment, the energy guide mover 129 can be positioned within or adjacent to the catheter shaft 110. Still alternatively, the energy guide mover 129 can be omitted, and movement of the energy guide(s) 122A in a proximal and/or distal direction and/or rotationally can be performed manually by a user of the catheter system 100.

As provided in greater detail herein, movement of the energy guide(s) 122A along the longitudinal axis 144 and/or rotationally about the longitudinal axis 144 can occur while sub-millisecond pulses of energy from the energy source 124 are also occurring. With this design, more complete plasma formation and bubble formation can occur within the balloon 104.

Figure 2:
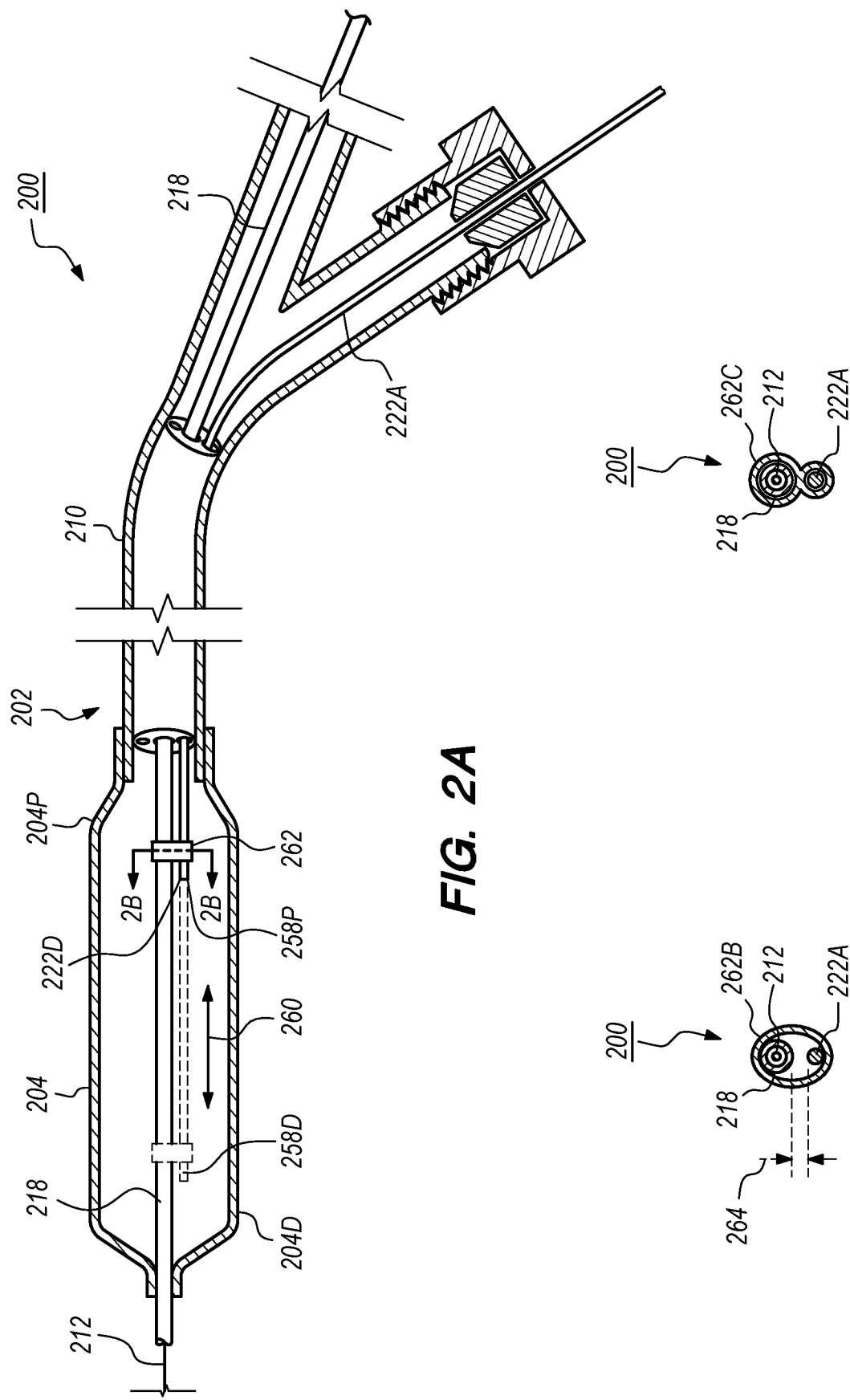
FIG. 2A is a schematic cross-sectional view of a portion of an embodiment of the catheter system.
FIG. 2B is a schematic cross-sectional view of a portion of the catheter system taken on line 2B-2B in FIG. 2A, including an embodiment of a guide coupler usable within the catheter system.
FIG. 2C is a schematic cross-sectional view of a portion of the catheter system including another embodiment of the guide coupler.

FIG. 2A is a schematic cross-sectional view of a portion of an embodiment of the catheter system 200. In particular, FIG. 2A illustrates the catheter 202, including the balloon 204, the catheter shaft 210, the guide shaft 218, and the guidewire 212, and an energy guide 222A. In the embodiment illustrated in FIG. 2A, the energy guide mover 129 (illustrated in FIG. 1) has been omitted for clarity, as have other structures. It is understood that although various structures are not illustrated in FIG. 2A, such structures can be included as part of the catheter system 200, or such structures can be omitted entirely from the catheter system 200.

As shown in the embodiment illustrated in FIG. 2A, the energy guide 222A is selectively movable and/or positionable such that the guide distal end 222D of the energy guide 222 can be selectively moved to and positioned at different locations within the balloon 204. More specifically, in this embodiment, the energy guide 222A can be moved so that the guide distal end 222D of the energy guide 222A is moved between a proximal position (shown as 258P) and a distal position (shown in phantom as 258D) in a direction illustrated by arrow 260. In this embodiment, movement of the energy guide 222A can occur while the energy guide 222A is receiving energy from the energy source 124 (illustrated in FIG. 1) to generate the plasma that creates the pressure waves within the balloon fluid 132 (illustrated in FIG. 1). Movement of the energy guide 222A and/or the guide distal end 222D between the proximal position 258P (near the balloon proximal end 204P) and the distal position 258D (near the balloon distal end 204D) can occur via the energy guide mover 129 (illustrated in FIG. 1) or manually by the operator.

In the embodiment illustrated in FIG. 2A, the energy guide 222A can be movably coupled to the guide shaft 218 with a guide coupler 262. The guide coupler 262 can be fixedly secured and/or adhered to the energy guide 222A. Further, the guide coupler 262 can be slidably or otherwise movably positioned about the guide shaft 218. With this design, movement of the energy guide 222A and/or the guide distal end 222D between the proximal position 258P and the distal position 258D maintains the energy guide 222A within a relatively close proximity to the guide shaft 218 so that the guide shaft 218 guides movement of the energy guide 222A within the balloon 204.

In an alternative embodiment, the guide coupler 262 can be fixedly secured and/or adhered to the guide shaft 218. In this alternative embodiment, the guide coupler 262 can be slidably or otherwise movably positioned about the energy guide 222A. Additionally, or in the alternative, the catheter 202 can include a plurality of guide couplers 262 to maintain a particular spacing (or no spacing) between the guide shaft 218 and the energy guide 222A.

In various embodiments, during movement of the energy guide 222A, as the guide distal end 222D of the energy guide 222A moves between the proximal position 258P and the distal position 258D, the energy guide 222A moves relative to the guide shaft 218, with such movement being guided by the guide coupler 262. Additionally, in some such embodiments, the guide shaft 218 can be substantially stationary during such movement of the energy guide 222A and/or the guide distal end 222D.

FIG. 2B is a schematic cross-sectional view of a portion of the catheter system 200 taken on line 2B-2B in FIG. 2A, including an embodiment of a guide coupler 262B. In the embodiment illustrated in FIG. 2B, the guide coupler 262B encircles at least a portion of the energy guide 222A and the guide shaft 218, which in turn, encircles the guidewire 212. As illustrated in this embodiment, the guide coupler 262B can maintain a spacing 264 between the energy guide 222A and the guide shaft 218, and/or can maintain such spacing 264 within a desired range.

FIG. 2C is a schematic cross-sectional view of a portion of the catheter system 200 including another embodiment of the guide coupler 262C. In this embodiment, the guide coupler 262C again encircles at least a portion of the energy guide 222A and the guide shaft 218, which in turn, encircles the guidewire 212. However, in this alternative embodiment, the guide coupler 262C maintains the energy guide 222A and the guide shaft 218 substantially adjacent to one another, and/or with the energy guide 222A and the guide shaft 218 fixed in position relative to one another, with a precise spacing (or no spacing) therebetween.

Figure 3:
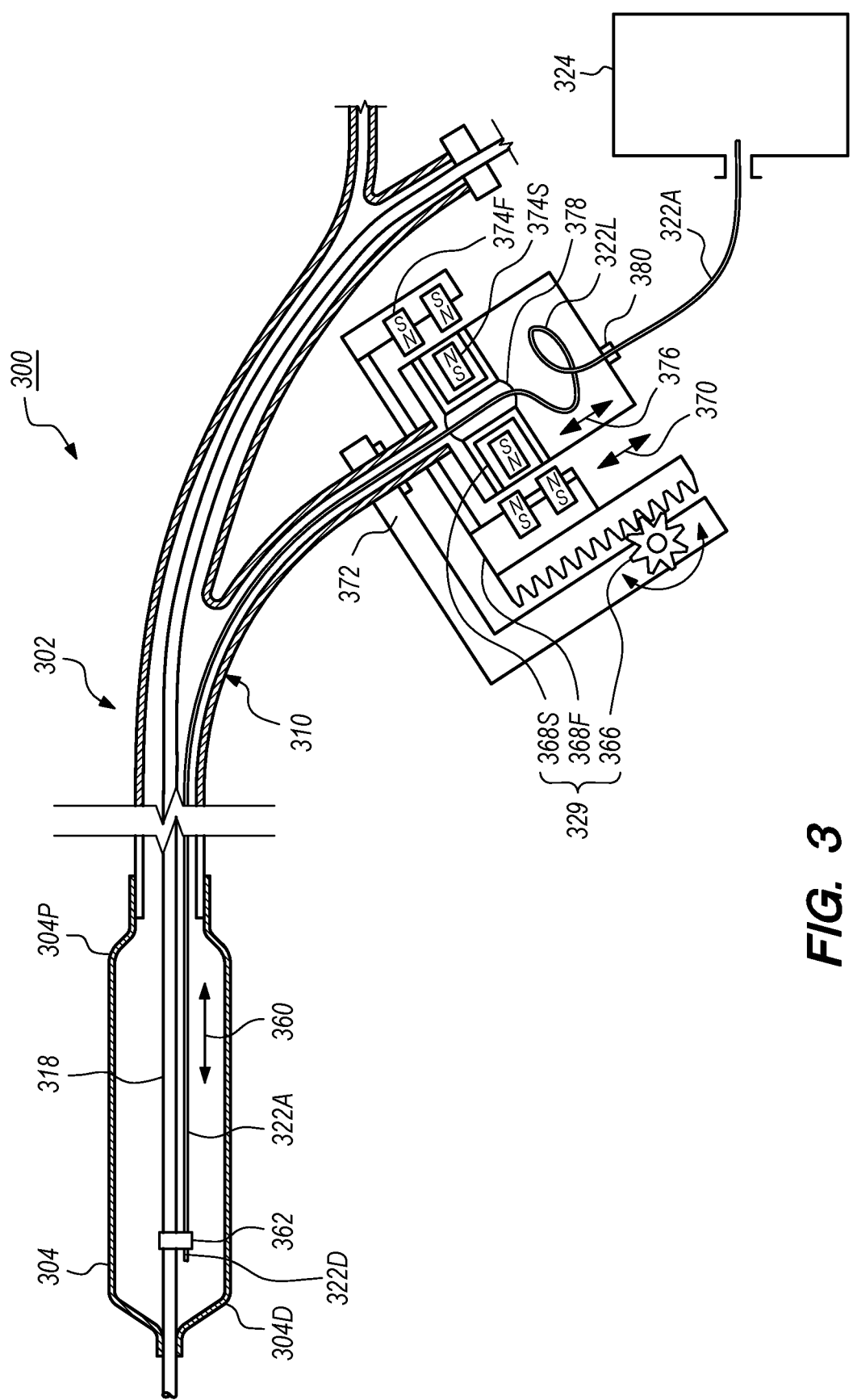
FIG. 3 is a schematic cross-sectional view of a portion of another embodiment of the catheter system.

FIG. 3 is a schematic cross-sectional view of a portion of another embodiment of the catheter system 300. In particular, FIG. 3 illustrates the catheter 302, including the balloon 304, the catheter shaft 310, and the guide shaft 318, and an energy guide 322A. Additionally, in the embodiment illustrated in FIG. 3, the catheter system 300 includes another embodiment of the energy guide mover 329.

Somewhat similarly to other embodiments provided herein, in the embodiment illustrated in FIG. 3, the energy guide 322A is selectively movable and/or positionable such that the guide distal end 322D of the energy guide 322A can be selectively moved to and positioned at different locations within the balloon 304. More specifically, in this embodiment, the energy guide 322A can be moved so that the guide distal end 322D of the energy guide 322A is moved between a proximal position (with the guide distal end 322D positioned near the balloon proximal end 304P) and a distal position (with the guide distal end 322D positioned near the balloon distal end 304D) in a direction illustrated by arrow 360. The energy guide 322A can be coupled to the guide shaft 318 via a guide coupler 362, which can be somewhat similar or identical to the guide coupler 262 previously described in relation to FIG. 2A. In this embodiment, movement of the energy guide 322A can occur while the energy guide 322A is receiving energy from the energy source 324 to generate the plasma that creates the pressure waves within the balloon fluid 132 (illustrated in FIG. 1. Movement of the energy guide 322A and/or the guide distal end 322D between the proximal position and the distal position can occur via the energy guide mover 329 or manually by the operator.

In this embodiment, the energy guide mover 329 can include a drive gear 366, a first mover member 368F and a second mover member 368S. In one non-exclusive embodiment, the drive gear 366 can be rotatably secured to a gear holder 372. In one non-exclusive embodiment, the gear holder 372 can be secured to another portion of the catheter 302 such as the catheter shaft 310. Alternatively, the gear holder 372 can be omitted, and the drive gear 366 can be directly secured to another portion of the catheter 302.

The drive gear 366 can rotatably engage the first mover member 368F to cause linear movement of the first mover member 368F in a direction illustrated by arrow 370. In one non-exclusive embodiment, the drive gear 366 and the first mover member 368F can be a rack and pinion type of arrangement. The first mover member 368F can include one or more first magnets 374F (four first magnets are illustrated in FIG. 3, although only one first magnet 374F is numerically identified). Further, the second mover member 368S can include one or more second magnets 374S (two second magnets are illustrated in FIG. 3, although only one second magnet 374S is numerically identified). The first mover member 368F and the second mover member 368S can magnetically cooperate with one another so that movement of the first mover member 368F by the drive gear 366 causes a corresponding linear movement of the second mover member 368S in a direction illustrated by arrow 376. In various embodiments, the second mover member 368S can be coupled to the energy guide 322A. Thus, in such embodiments, linear movement of the second mover member 368S moves the energy guide 322A linearly back and/or forth along the direction illustrated by arrow 360, e.g. between the proximal position where the guide distal end 322D is positioned near the balloon proximal end 304P and the distal position where the guide distal end 322D is positioned near the balloon distal end 304D.

In the embodiment illustrated in FIG. 3, the energy guide 322A includes an access loop 322L. The access loop 322L provides extra length to the energy guide 322 so that movement of the second mover member 350S in a back-and-forth motion provides for, or uses, slack of the access loop 322L. In this embodiment, the second mover member 368S can also include a guide holder 378 that fixedly holds the energy guide 322A to the second mover member 368S near a distal end of the access loop 322L. Additionally, in the embodiment illustrated in FIG. 3, the energy guide 322A can also be fixedly secured to a portion of a second member housing 380 near a proximal end of the access loop 322L.

Figure 4:
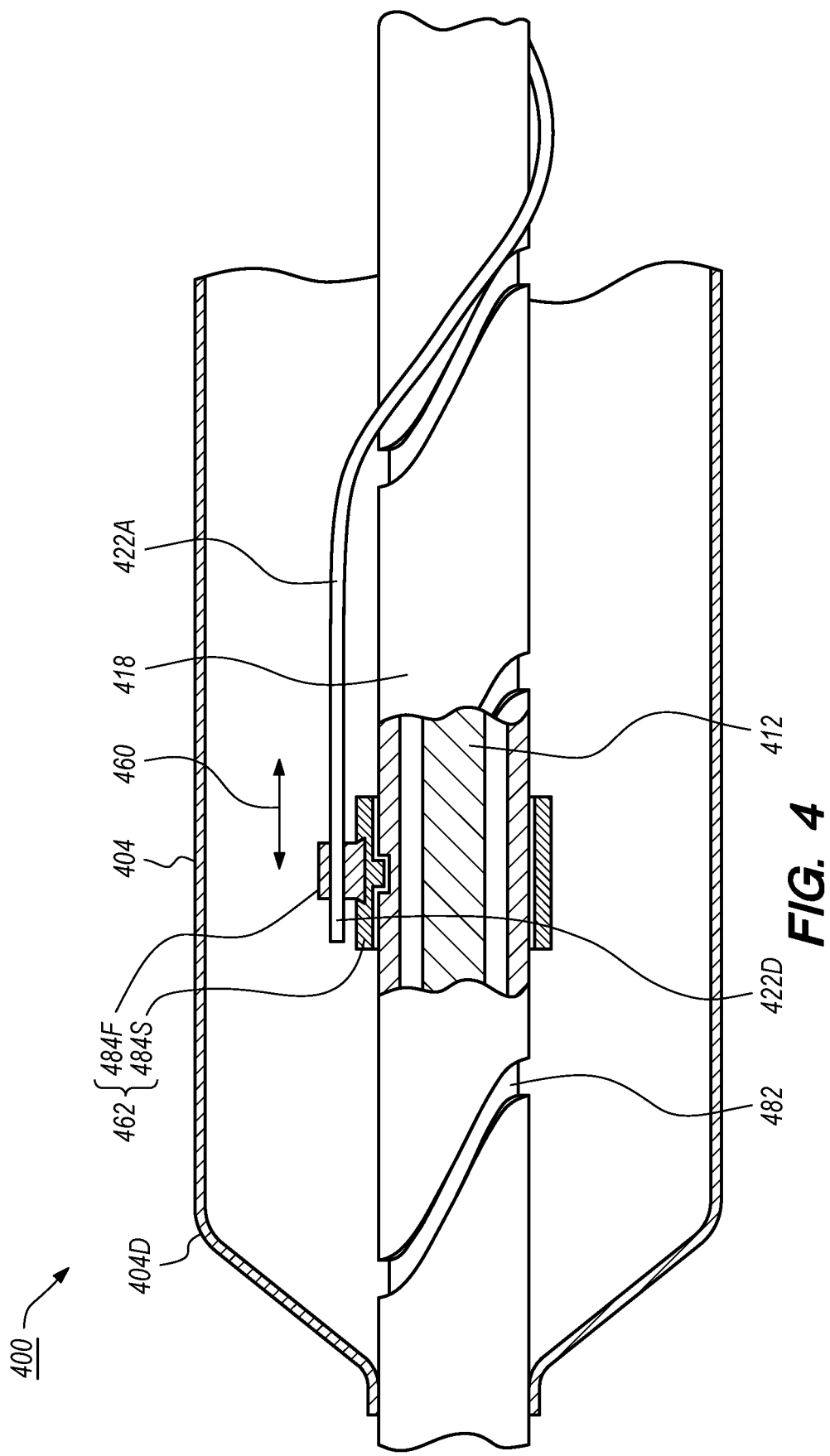
FIG. 4 is a schematic cross-sectional view of a portion of yet another embodiment of the catheter system.

FIG. 4 is a schematic cross-sectional view of a portion of yet another embodiment of the catheter system 400. As with the previous embodiments, the energy guide 422A is selectively movable and/or positionable such that the guide distal end 422D of the energy guide 422A can be selectively moved to and positioned at different locations within the balloon 404. More specifically, in this embodiment, the energy guide 422A can again be moved so that the guide distal end 422D of the energy guide 422A is moved between a proximal position (with the guide distal end 422D positioned near the balloon proximal end (not shown in FIG. 4)) and a distal position (with the guide distal end 422D positioned near the balloon distal end 404D) in a direction illustrated by arrow 460.

In this embodiment, the energy guide 422A can again be movably coupled to the guide shaft 418 via a guide coupler 462. In this embodiment, the guide shaft 418 can encircle at least a portion of the guidewire 412, and can include a guide channel 482 that can have a somewhat spiral configuration about the guide shaft 418. Alternatively, the guide channel 482 can have another suitable configuration.

In the embodiment illustrated in FIG. 4, the guide coupler 462 can include a first coupler member 484F and a second coupler member 484S that is secured to the first coupler member 484F. The first coupler member 484F can be secured to the energy guide 422A such as by an adhesive (not shown) in one non-exclusive embodiment. The second coupler member 484S can be movably secured to the guide channel 482 of the guide shaft 418 or another suitable structure within the balloon 404. In this embodiment, the second coupler member 484S can movably engage the guide channel 482 so that the second coupler member 484S remains secured to the guide channel 482 during movement of the second coupler member 484S in a direction (illustrated by arrow 460) between the balloon distal end 404D and the balloon proximal end within the balloon 404. In an alternative embodiment, the first coupler member 484F and the second coupler member 484S can be integrally formed as a unitary structure.

In the embodiment illustrated in FIG. 4, as the energy guide 422A is moved by the energy guide mover (not shown in FIG. 4) in direction 460 between the balloon distal end 404D and the balloon proximal end, the second coupler member 484S can rotate and move in a somewhat spiral motion about the guide shaft 418. The guide distal end 422D of the energy guide 422A can be positioned at any suitable angle relative to the guide shaft 418 and/or the balloon 404. In the embodiment illustrated in FIG. 4, the guide distal end 422D of the energy guide 422A is approximately parallel to the guide shaft 418. Alternatively, the guide distal end 422D of the energy guide 422A can be angled away from the guide shaft 418 and/or in a direction that is more directed toward the balloon 404.

In one embodiment, the guide channel 482 can be configured to allow for at least one full 360-degree rotation of the second coupler member 484S and the first coupler member 484F, and thus, the energy guide 422A, about the guide shaft 418 during movement of the energy guide 422A between the distal position near the balloon distal end 404D and the proximal position near the balloon proximal end. With this design, energy from the energy source (not shown in FIG. 4) can be more evenly dispersed and/or distributed to a circumference of the balloon 404 to disrupt any vascular lesions 106A (illustrated in FIG. 1) at the treatment site 106 (illustrated in FIG. 1) within or on a blood vessel 108 (illustrated in FIG. 1). Alternatively, the guide channel 482 can be configured to allow for less than one full 360-degree rotation of the second coupler member 484S and the first coupler member 484F, and thus, the energy guide 422A, about the guide shaft 418 during movement of the energy guide 422A between the distal position near the balloon distal end 404D and the proximal position near the balloon proximal end.

Figure 5:
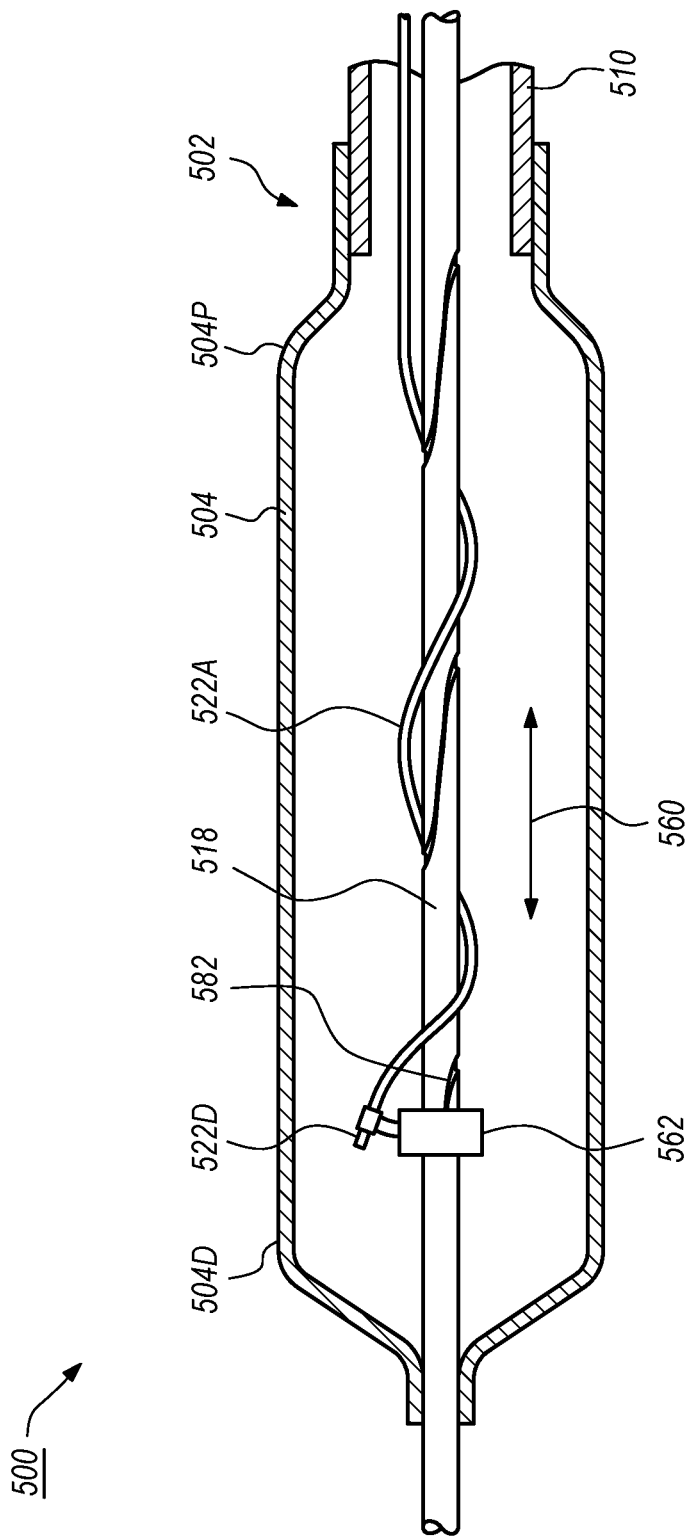
FIG. 5 is a schematic cross-sectional view of a portion of still another embodiment of the catheter system.

FIG. 5 is a schematic cross-sectional view of a portion of still another embodiment of the catheter system 500. In particular, FIG. 5 illustrates the catheter 502, including the balloon 504, the catheter shaft 510, and the guide shaft 518, and an energy guide 522A.

As with the previous embodiments, in the embodiment illustrated in FIG. 5, the energy guide 522A is selectively movable and/or positionable such that the guide distal end 522D of the energy guide 522A can be selectively moved to and positioned at different locations within the balloon 504. More specifically, in this embodiment, the energy guide 522A can again be moved so that the guide distal end 522D of the energy guide 522A is moved between a proximal position (with the guide distal end 522D positioned near the balloon proximal end 504P) and a distal position (with the guide distal end 522D positioned near the balloon distal end 504D) in a direction illustrated by arrow 560.

In this embodiment, the energy guide 522A can again be movably coupled to the guide shaft 518 via a guide coupler 562. In this embodiment, the guide shaft 518 can also include a guide channel 582 that can have a somewhat spiral configuration about the guide shaft 518. Alternatively, the guide channel 582 can have another suitable configuration.

In the embodiment illustrated in FIG. 5, the guide coupler 562 can operate and be configured substantially similarly to other embodiments of the guide coupler shown and described herein. For example, in the embodiment illustrated in FIG. 5, as the energy guide 522A is moved by the energy guide mover (not shown in FIG. 5) in direction 560 between the distal position near the balloon distal end 504D and the proximal position near the balloon proximal end 504P, the guide coupler 562 can rotate and move in a somewhat spiral motion about the guide shaft 518. The guide distal end 522D of the energy guide 522A can be positioned at any suitable angle relative to the guide shaft 518 and/or the balloon 504. In the embodiment illustrated in FIG. 5, the guide distal end 522D of the energy guide 522A is angled away from the guide shaft 518 and/or in a direction that is more directed toward the balloon 504.

FIG. 6 is a schematic cross-sectional view of a portion of yet another embodiment of the catheter system 600. In particular, FIG. 6 illustrates the catheter 602, including the balloon 604, the catheter shaft 610, the guide shaft 618, and the guidewire 612, and an energy guide 622A.

As with the previous embodiments, in the embodiment illustrated in FIG. 6, the energy guide 622A is again selectively movable and/or positionable such that the guide distal end 622D of the energy guide 622A can be selectively moved to and positioned at different locations within the balloon 604. More specifically, in this embodiment, the energy guide 622A can be moved so that the guide distal end 622D of the energy guide 622A is moved between a proximal position (with the guide distal end 622D positioned near the balloon proximal end 604P) and a distal position (with the guide distal end 622D positioned near the balloon distal end 604D) in a direction illustrated by arrow 660.

In this embodiment, the energy guide 622 can again be movably coupled to the guide shaft 618 via a guide coupler 662. In this embodiment, the guide shaft 618 can also include a guide channel 682 that can have a somewhat spiral configuration about the guide shaft 618. However, in this embodiment, the guide channel 682 is inverted from the previously shown and described guide channels 482 (illustrated in FIG. 4), 582 (illustrated in FIG. 5). Stated in another manner, rather than the guide channel 682 being disposed within the guide shaft 618 and extending inwardly toward the guidewire 612, in this embodiment the guide channel 682 extends outwardly away from the guidewire 612 as a raised channel.

In the embodiment illustrated in FIG. 6, the guide coupler 662 can include a first coupler member 684F and a second coupler member 684S that is secured to the first coupler member 684F. The first coupler member 684F can be secured to the energy guide 622A, such as by an adhesive (not shown) in one non-exclusive embodiment. The second coupler member 684S can be movably secured to the guide channel 682 of the guide shaft 618 or to another suitable structure within the balloon 604. In this embodiment, the second coupler member 684S can movably engage the guide channel 682 so that the second coupler member 684S remains secured to the guide channel 682 during movement of the second coupler member 684S in direction 660 between the distal position near the balloon distal end 604D and the proximal position near the balloon proximal end 604P within the balloon 604. In an alternative embodiment, the first coupler member 684F and the second coupler member 684S can be integrally formed as a unitary structure.

In the embodiment illustrated in FIG. 6, as the energy guide 622A is moved by the energy guide mover (not shown in FIG. 6) in direction 660 between the balloon distal end 604D and the balloon proximal end 604P, the second coupler member 684S can rotate and move in a somewhat spiral motion about the guide shaft 618. The guide distal end 622D of the energy guide 622A can be positioned at any suitable angle relative to the guide shaft 618 and/or the balloon 604. In the embodiment illustrated in FIG. 6, the guide distal end 622D of the energy guide 622A is approximately parallel to the guide shaft 618. Alternatively, the guide distal end 622D of the energy guide 622A can be angled away from the guide shaft 618 and/or in a direction that is more directed toward the balloon 604.

In one embodiment, the guide channel 682 can be configured to allow for at least one full 360-degree rotation of the second coupler member 684S and the first coupler member 684F, and thus, the energy guide 622A, about the guide shaft 618 during movement of the energy guide 622A between the balloon distal end 604D and the balloon proximal end 604P. With this design, energy can be more evenly dispersed and/or distributed to a circumference of the balloon 604 to disrupt any vascular lesions 106A (illustrated in FIG. 1) at the treatment site 106 (illustrated in FIG. 1) within or on a blood vessel 108 (illustrated in FIG. 1). Alternatively, the guide channel 682 can be configured to allow for less than one full 360-degree rotation of the second coupler member 684S and the first coupler member 684F, and thus, the energy guide 622A, about the guide shaft 618 during movement of the energy guide 622A between the balloon distal end 604D and the balloon proximal end 604P.

FIG. 7 is a schematic side view of a portion of another embodiment of the catheter system 700. In particular, FIG. 7 only illustrates a portion of the guide shaft 718, and a guide channel 782 that is formed onto and/or extends outwardly away from the guide shaft 718.

In this embodiment, the guide channel 782 has a somewhat sinusoidal configuration. Although the guide channel 782 illustrated in FIG. 7 extends outwardly from the guide shaft 718 as a raised channel, the guide channel 782 can equally extend inwardly into the guide shaft 718. With this sinusoidal design of the guide channel 782, the energy guide (not shown in FIG. 7) can move in a back-and-forth motion in order for the energy to impart pressure waves more completely around the circumference of the balloon (not shown in FIG. 7) than if the energy guide simply moved linearly along the guide shaft 718.

Examples of the catheters in accordance with various embodiments include those having multiple energy guides disposed about the catheter shaft and/or the guide shaft at different positions around the circumference, as shown in FIGS. 8-11.

Figure 8:
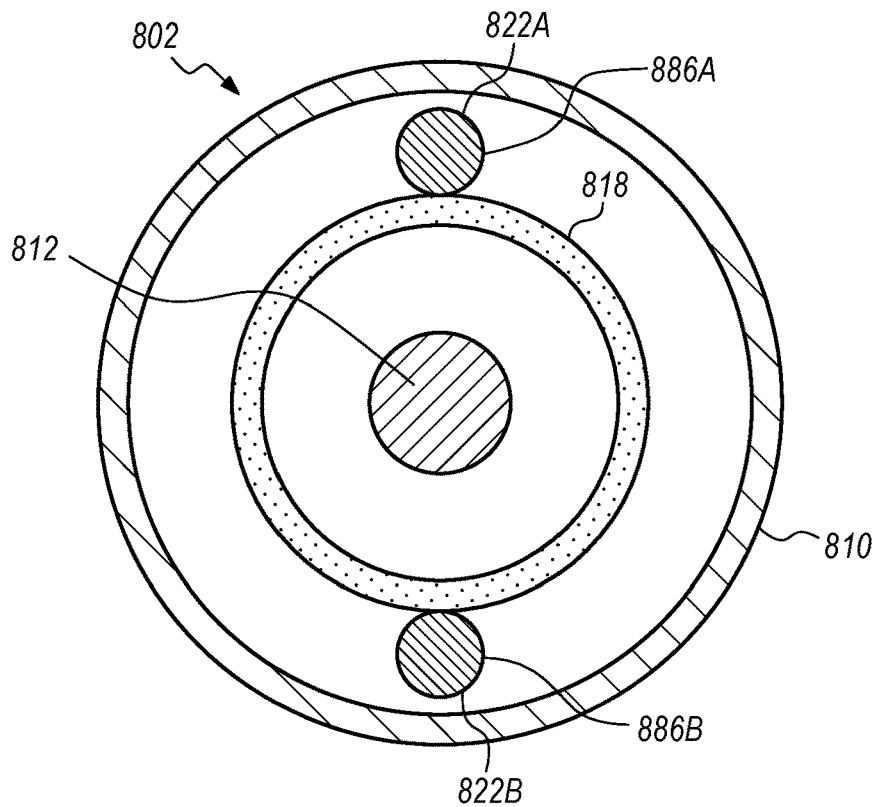
FIG. 8 is a schematic cross-sectional view of the catheter system taken on line 8-8 in FIG. 1.

Referring now to FIG. 8, a schematic cross-sectional view of the catheter 102 in FIG. 1 along line 8-8 in FIG. 1 is shown in accordance with various embodiments. In particular, as shown in FIG. 8, the catheter 802 includes a catheter shaft 810, a guide shaft 818, a guidewire 812, and a first energy guide 822A and a second energy guide 822B that are separated from one another by approximately 180 degrees around a circumference of the catheter shaft 810 and/or the guide shaft 818.

As illustrated, the first energy guide 822A includes a side surface 886A that can include any surface portion about a circumference of the first energy guide 822A. The second energy guide 822B includes a side surface 886B that can include any surface portion about the circumference of the second energy guide 822B. In some embodiments, the side surface 886A, 886B of each energy guide 822A, 822B spans a portion of the circumference of the energy guide 822A, 822B, such that it is less than cylindrical. In other embodiments, the side surface 886A, 886B of each energy guide 822A, 822B can span the entire circumference of the energy guide 822A, 822B such that it is cylindrical. It is recognized that any energy guide described herein can include a side surface about the circumference of the energy guide.

Figure 9:
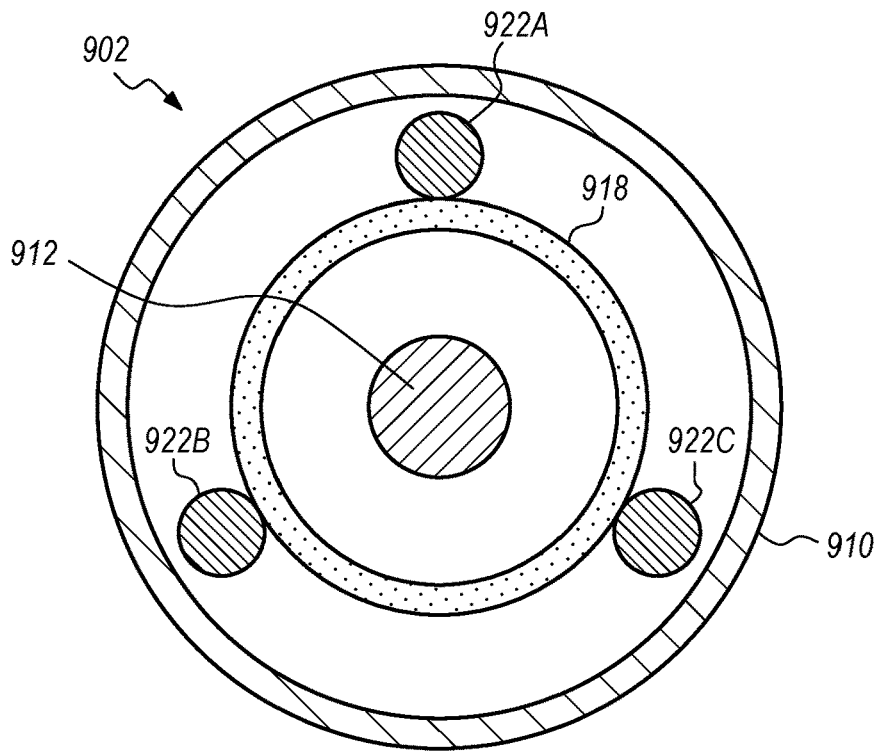
FIG. 9 is a schematic cross-sectional view of another embodiment of the catheter system.
Figure 10:
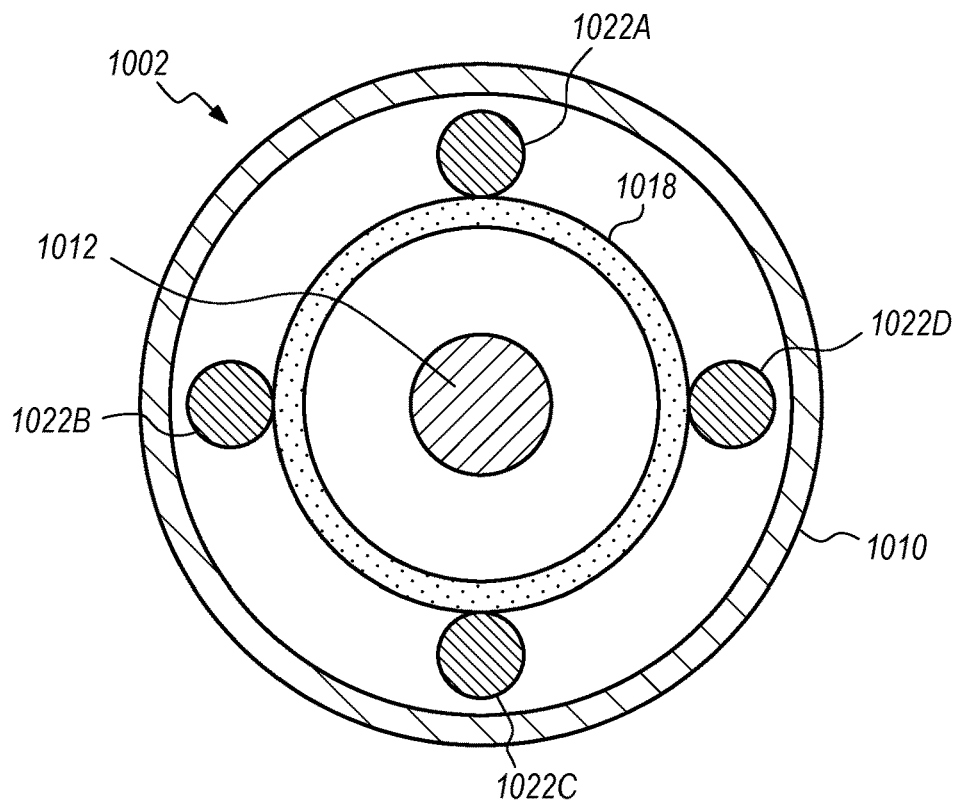
FIG. 10 is a schematic cross-sectional view of yet another embodiment of the catheter system.
Figure 11:
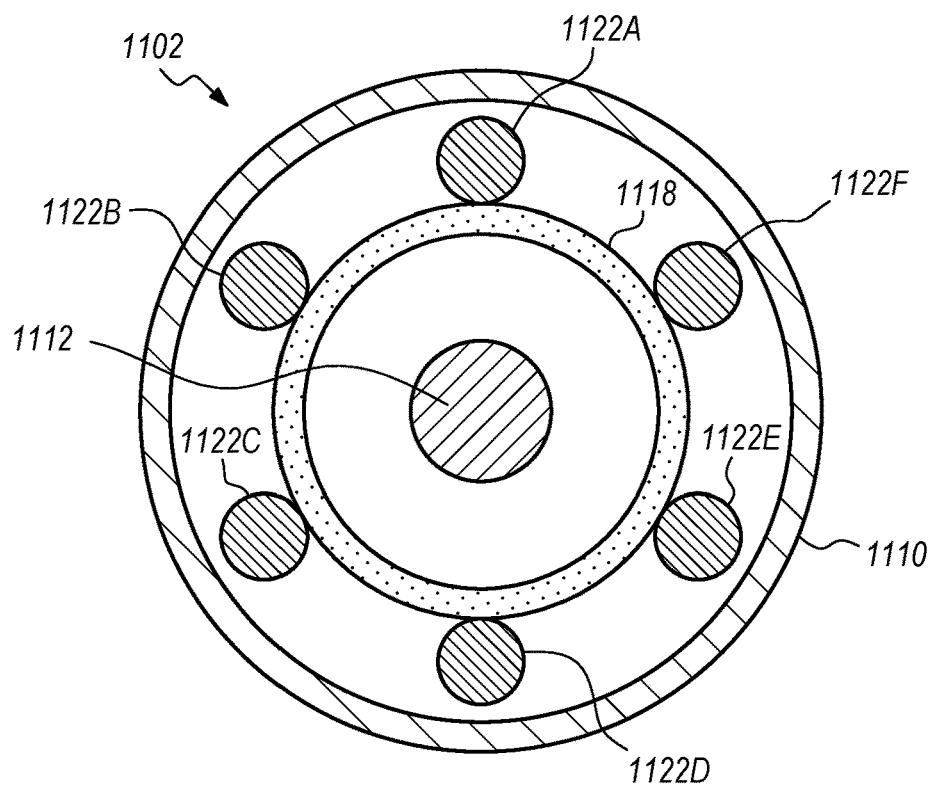
FIG. 11 is a schematic cross-sectional view of still another embodiment of the catheter system.

Referring now to FIGS. 9-11, schematic cross-sectional views of additional configurations for catheters having multiple energy guides are shown in accordance with various embodiments.

The configuration of the catheter 902 in FIG. 9 includes a catheter shaft 910, a guidewire 912, a guide shaft 918, and a first energy guide 922A, a second energy guide 922B, and a third energy guide 922C that are separated from one another by approximately 120 degrees around a circumference of the catheter shaft 910 and/or the guide shaft 918.

The configuration of the catheter 1002 in FIG. 10 includes a catheter shaft 1010, a guidewire 1012, a guide shaft 1018, and a first energy guide 1022A, a second energy guide 1022B, a third energy guide 1022C, and a fourth energy guide 1022D that are separated from one another by approximately 90 degrees around the circumference of the catheter shaft 1010 and/or the guide shaft 1018.

The configuration of catheter 1102 shown in FIG. 11 includes a catheter shaft 1110, a guidewire 1112, a guide shaft 1118, and a first energy guide 1122A, a second energy guide 1122B, a third energy guide 1122C, a fourth energy guide 1122D, a fifth energy guide 1122E, and a sixth energy guide 1122F that are separated from one another by approximately 60 degrees around the circumference of the catheter shaft 1110 and/or the guide shaft 1118.

It is understood that greater than six energy guides can be used in certain embodiments. It is further appreciated that the energy guides can be disposed uniformly or nonuniformly about the catheter shaft and/or the guide shaft to achieve the desired effect in the desired locations.

As noted above, FIGS. 12-15 illustrate certain non-exclusive alternative embodiments of the guide distal end of the energy guide, which can include one or more photoacoustic transducers and/or one or more diverting features.

Figure 12:
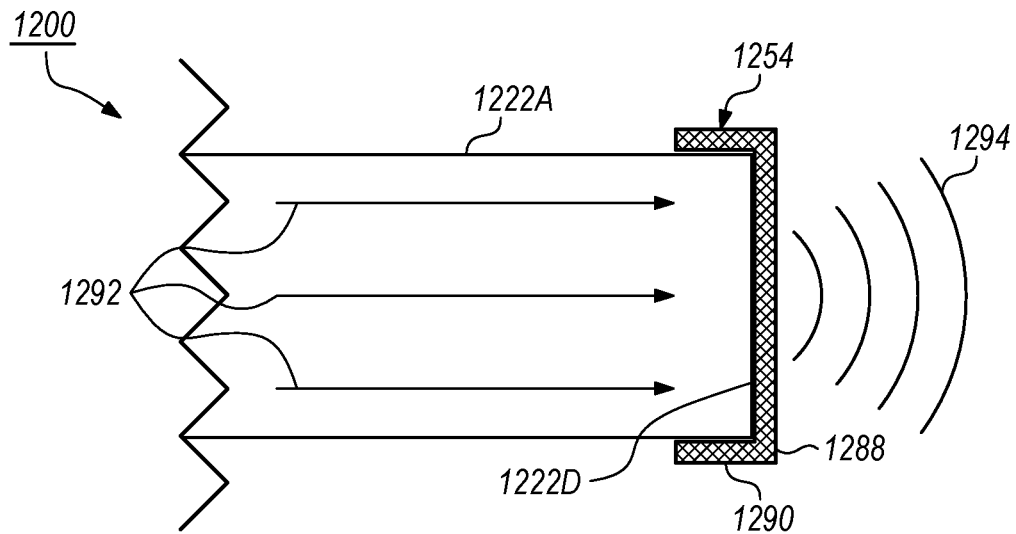
FIG. 12 is a schematic cross-sectional view of a portion of the catheter system including an embodiment of a guide distal end of an energy guide.

Referring initially to FIG. 12, FIG. 12 is a schematic cross-sectional view of a portion of the catheter system 1200 including an embodiment of the guide distal end 1222D of the energy guide 1222A. In this embodiment, as shown, the catheter system 1200 includes a photoacoustic transducer 1254 that is disposed at the guide distal end 1222D of the energy guide 1222A, and which is in optical communication with the energy guide 1222A within which it is disposed.

The shape of the guide distal end 1222D of the energy guide 1222A, and the shape of the photoacoustic transducer 1254 can be varied. In this embodiment, the guide distal end 1222D of the energy guide includes a substantially cylindrical shape. The photoacoustic transducer 1254 also has a cylindrical shape that corresponds and/or conforms with the shape of the guide distal end 1222D of the energy guide 1222A. As illustrated, the photoacoustic transducer 1254 can include a circular end face 1288 and a cylindrical sidewall 1290, where the cylindrical sidewall 1290 is approximately at a 90 degree angle to the circular end face 1288. The energy guide 1222A is configured such that energy 1292, e.g., light energy, travels from the energy source 124 (illustrated in FIG. 1), e.g., light source, in a direction from the guide proximal end 122P (illustrated in FIG. 1) to the guide distal end 1222D, as indicated by arrows 1292. The energy 1292 within the energy guide 1222A is directed to the photoacoustic transducer 1254, which converts light energy into an acoustic wave 1294 at the guide distal end 1222D of the energy guide 1222A.

Figure 13:
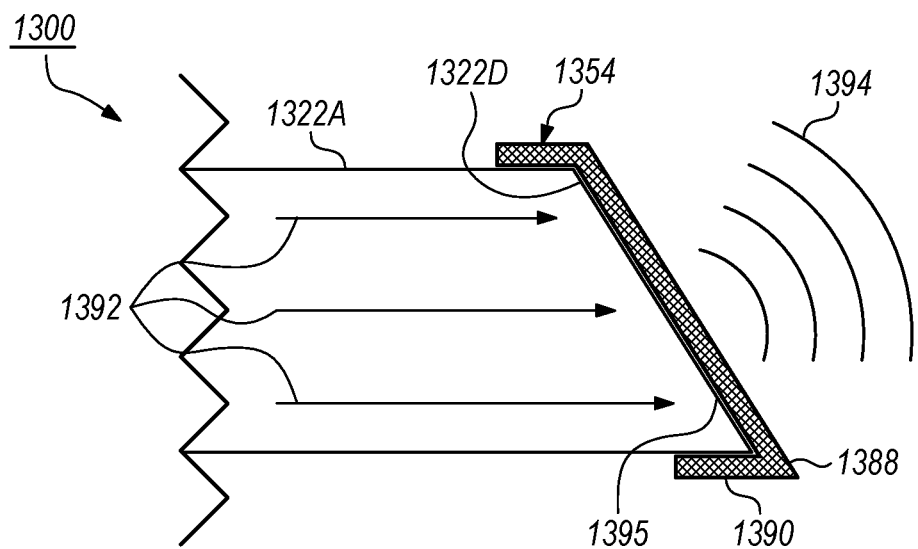
FIG. 13 is a schematic cross-sectional view of a portion of the catheter system including another embodiment of the guide distal end of the energy guide.

FIG. 13 is a schematic cross-sectional view of a portion of the catheter system 1300 including another embodiment of the guide distal end 1322D of the energy guide 1322A. As with the previous embodiment, the catheter system 1300 again includes a photoacoustic transducer 1354 that is disposed at the guide distal end 1322D of the energy guide 1322A, and which is in optical communication with the energy guide 1322A within which it is disposed.

In this embodiment, the energy guide 1322A includes an angled end 1395 having an angled shape. The photoacoustic transducer 1354 also has an angled shape that corresponds and/or conforms to the angled end 1395 of the energy guide 1322A. In particular, the photoacoustic transducer 1354 includes an angled end face 1388 and a cylindrical side wall 1390 extending from the angled end face 1388. The energy guide 1322A is configured such that energy 1392, e.g., light energy, travels from the energy source 124 (illustrated in FIG. 1), e.g., light source, in a direction from the guide proximal end 122P (illustrated in FIG. 1) to the guide distal end 1322D, as indicated by arrows 1392. The energy 1392 within the energy guide 1322A is directed to the photoacoustic transducer 1354, which converts light energy into an acoustic wave 1394 at the guide distal end 1322D of the energy guide 1322A. It is appreciated that the direction of the acoustic wave 1394 can be tailored by changing the angle of the angled end 1395 of the energy guide 1322A.

Figure 14:
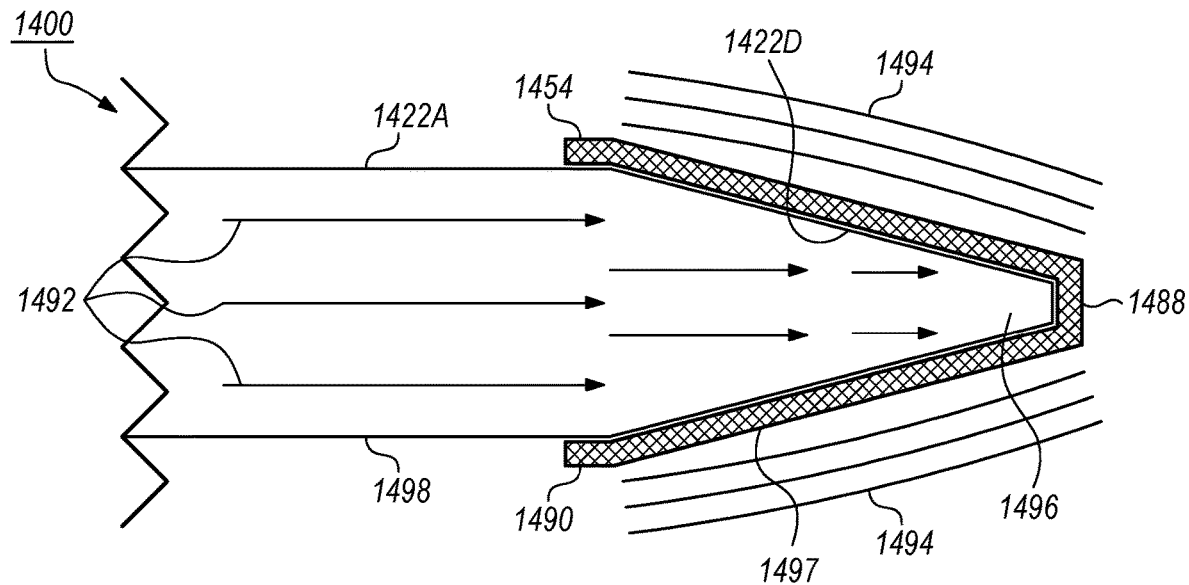
FIG. 14 is a schematic cross-sectional view of a portion of the catheter system including still another embodiment of the guide distal end of the energy guide.

FIG. 14 is a schematic cross-sectional view of a portion of the catheter system 1400 including still another embodiment of the guide distal end 1422D of the energy guide 1422A. As with the previous embodiments, the catheter system 1400 again includes a photoacoustic transducer 1454 that is disposed at the guide distal end 1422D of the energy guide 1422A, and which is in optical communication with the energy guide 1422A within which it is disposed.

However, in this embodiment, the energy guide 1422A includes a tapered end 1496 having a tapered shape. The photoacoustic transducer 1454 also has a tapered shape that corresponds and/or conforms to the tapered end 1496 of the energy guide 1422A. In particular, the photoacoustic transducer 1454 includes a circular end face 1488 and an angled sidewall 1497 converging at one end to the circular end face 1488. At an opposite end of the angled sidewall 1497, the photoacoustic transducer 1454 includes a cylindrical sidewall 1490 that is parallel with a side surface 1498 of the energy guide 1422A. The energy guide 1422A is configured such that energy 1492, e.g., light energy, travels from the energy source 124 (illustrated in FIG. 1), e.g., light source, in a direction from the guide proximal end 122P (illustrated in FIG. 1) to the guide distal end 1422D, as indicated by arrows 1492. The energy 1492 within the energy guide 1422A is directed to the photoacoustic transducer 1454, which converts light energy into an acoustic wave 1494 at the guide distal end 1422D of the energy guide 1422A. It is appreciated that with the tapered shape of the energy guide 1422A, the conical shape of the photoacoustic transducer 1454 can create an acoustic wave 1494 that can extend radially about the tapered end 1496 of the energy guide 1422A.

Figure 15:
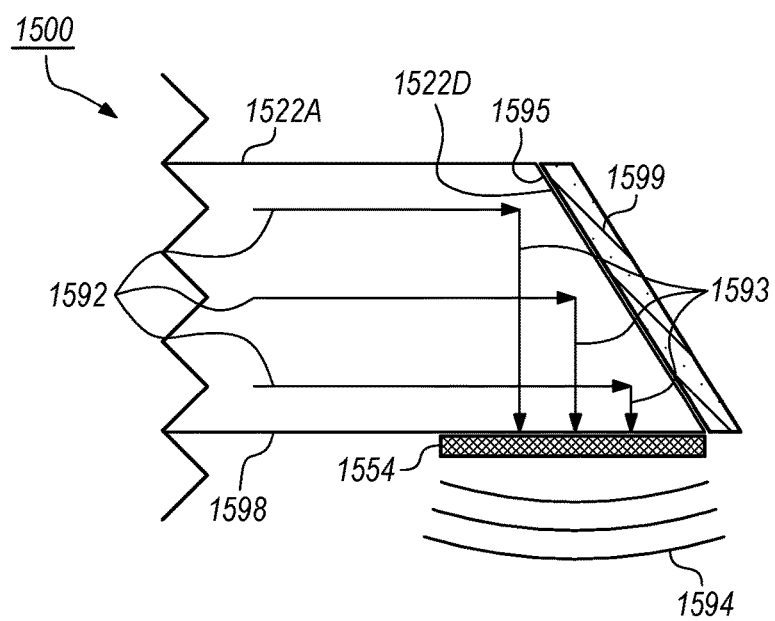
FIG. 15 is a schematic cross-sectional view of a portion of the catheter system including yet another embodiment of the guide distal end of the energy guide.

FIG. 15 is a schematic cross-sectional view of a portion of the catheter system 1500 including yet another embodiment of the guide distal end 1522D of the energy guide 1522A. As with the previous embodiments, the catheter system 1500 again includes a photoacoustic transducer 1554 that is disposed at the guide distal end 1522D of the energy guide 1522A, and which is in optical communication with the energy guide 1522A within which it is disposed.

In this embodiment, the energy guide 1522A includes an angled end 1595 having a photoacoustic transducer 1548 disposed on a side surface 1562 of a distal end 1564 of the energy guide 1522. However, in this embodiment, the energy guide 1522A also includes a diverting feature 1599 at the guide distal end 1522D to direct the energy 1592, e.g., light energy, within the energy guide 1522A toward the side surface 1598 of the energy guide 1522A at the site of the photoacoustic transducer 1554. The energy guide 1522A is configured such that energy 1592 travels from the guide distal end 1522D in a direction that is approximately 90 degrees (or another suitable angle) from the longitudinal axis 144 (illustrated in FIG. 1) as indicated by arrows 1593. Upon contact with the diverting feature 1599, the energy 1592 is diverted, or reflected, within the energy guide 1522A to the photoacoustic transducer 1554 that is in optical communication with a side surface 1598 of the energy guide 1522A. The photoacoustic transducer 1554 converts light energy into an acoustic wave 1594 that extends away from the side surface 1598 of the energy guide 1522A.

The diverting feature 1599 can have any suitable design for purposes of redirecting the energy 1592 within the energy guide 1522A as desired. For example, in certain non-exclusive embodiments, the diverting feature 1599 of energy guide 1522A can be made from a reflecting element or a refracting element. The diverting feature 1599 can be made from a glass, a polymer, a mirror, or a reflective metal coating. It is appreciated that the angle of internal reflection by the diverting feature 1599 can be adjusted by changing the angle of the guide distal end 1522D of energy guide 1522A. It is further appreciated that the side surface 1598 of the energy guide 1522A interfaces with the photoacoustic transducer 1554.

With the designs shown and described herein, movement of the energy guide between the balloon distal end and the balloon proximal end during emission of energy from the energy guide can increase the likelihood of disruption of a greater area of the intravascular lesion(s) to induce fractures in the lesion(s) that are in contact with, or in close proximity with any portion along a length of the balloon.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a blood vessel within a body of a patient, the treatment site having a proximal region and a distal region, the catheter system comprising:
    an energy source that generates energy, the energy source being configured to generate a plasma, causing rapid bubble formation that imparts pressure waves upon the treatment site;
    a guide shaft that is positionable adjacent to the treatment site;
    a catheter shaft that is configured to be selectively positioned near the treatment site, the guide shaft being positioned at least partially within the catheter shaft;
    an inflatable balloon that is coupled to the catheter shaft, the inflatable balloon including a balloon wall that defines a balloon interior, the inflatable balloon being configured to retain a balloon fluid within the balloon interior; and
    an energy guide that receives energy from the energy source, the energy guide being movably coupled to the guide shaft, the energy guide including a guide distal end that is configured to be positioned within the balloon interior and adjacent to the treatment site, the guide distal end of the energy guide being selectively movable relative to the balloon and the guide shaft and adjacent to and between the proximal region and the distal region of the treatment site while the energy guide receives energy from the energy source, the energy guide guiding the energy from the energy source so that the plasma generation is initiated in the balloon fluid within the balloon interior, the guide distal end of the energy guide being in fluid communication with the balloon fluid in which the plasma is generated.

2. The catheter system of claim 1 further comprising an energy guide mover that selectively moves the energy guide so that the guide distal end of the energy guide moves adjacent to and between the proximal region and the distal region of the treatment site while the energy guide receives energy from the energy source.

3. The catheter system of claim 2 wherein the energy guide mover includes a motorized roller that engages the energy guide, the motorized roller selectively moving the energy guide adjacent to and between the proximal region and the distal region of the treatment site while the energy guide receives energy from the energy source.

4. The catheter system of claim 2 wherein the energy guide mover includes a plurality of motorized rollers that engage the energy guide, the motorized rollers selectively moving the energy guide adjacent to and between the proximal region and the distal region of the treatment site while the energy guide receives energy from the energy source.

5. The catheter system of claim 1 wherein the energy guide is configured to be manually moved by an operator of the catheter system so that the guide distal end of the energy guide moves adjacent to and between the proximal region and the distal region of the treatment site while the energy guide receives energy from the energy source.

6. The catheter system of claim 1 wherein the guide shaft includes a guide channel that guides movement of the energy guide relative to the guide shaft.

7. The catheter system of claim 6 wherein the guide channel has a somewhat spiral configuration along a length of the guide shaft; and wherein the guide distal end of the energy guide moves in a substantially spiral manner while the guide distal end moves adjacent to and between the proximal region and the distal region of the treatment site.

8. The catheter system of claim 6 wherein the guide channel has a somewhat sinusoidal configuration along a length of the guide shaft; and wherein the guide distal end of the energy guide moves in a substantially sinusoidal manner while the guide distal end moves adjacent to and between the proximal region and the distal region of the treatment site.

9. The catheter system of claim 1 wherein the inflatable balloon is selectively inflatable with the balloon fluid to expand to an inflated state, wherein when the inflatable balloon is in the inflated state the balloon wall is configured to be positioned substantially adjacent to the treatment site.

10. The catheter system of claim 1 wherein the inflatable balloon is selectively inflatable with the balloon fluid to expand to an inflated state; and wherein the energy source is a light source that is configured to provide sub-millisecond pulses of light energy to the energy guide so that the plasma generation is initiated in the balloon fluid within the balloon interior that has been used to expand the inflatable balloon to the inflated state.

11. The catheter system of claim 10 wherein the energy guide includes an optical fiber that is configured to guide the light energy from the light source from a guide proximal end to the guide distal end.

12. The catheter system of claim 10 wherein the energy guide includes a photoacoustic transducer that converts the light energy into an acoustic wave near the distal end of the energy guide.

13. The catheter system of claim 1 wherein the energy guide includes a diverting feature that directs the energy toward a side surface of the guide distal end of the energy guide.

14. The catheter system of claim 1 wherein the inflatable balloon includes a drug eluting coating.

15. A catheter system for treating a treatment site within or adjacent to a blood vessel within a body of a patient, the treatment site having a proximal region and a distal region, the catheter system comprising:
 an energy source that generates energy, the energy source being configured to generate a plasma, causing rapid bubble formation that imparts pressure waves upon the treatment site;
 a guide shaft that is positionable adjacent to the treatment site, the guide shaft including a guidewire lumen that encircles a guidewire;
 a catheter shaft that is configured to be selectively positioned near the treatment site, the guide shaft being positioned at least partially within the catheter shaft;
 an inflatable balloon that is coupled to the catheter shaft, the inflatable balloon including a balloon wall that defines a balloon interior, the inflatable balloon being configured to retain a balloon fluid within the balloon interior;
 an energy guide that receives energy from the energy source, the energy guide being movably coupled to the guide shaft, the energy guide including a guide distal end that is configured to be positioned within the balloon interior and adjacent to the treatment site, the guide distal end of the energy guide being selectively movable relative to the balloon and the guide shaft and adjacent to and between the proximal region and the distal region of the treatment site while the energy guide receives energy from the energy source, the energy guide guiding the energy from the energy source so that the plasma generation is initiated in the balloon fluid within the balloon interior, the guide distal end of the energy guide being in fluid communication with the balloon fluid in which the plasma is generated; and
 an energy guide mover that selectively moves the energy guide so that the guide distal end of the energy guide moves adjacent to and between the proximal region and the distal region of the treatment site while the energy guide receives energy from the energy source.

16. The catheter system of claim 15 wherein the energy guide mover includes a motorized roller that engages the energy guide, the motorized roller selectively moving the energy guide adjacent to and between the proximal region and the distal region of the treatment site while the energy guide receives energy from the energy source.

17. The catheter system of claim 15 wherein the energy guide mover is one of hydraulically powered, pneumatically powered, electrically powered, magnetically powered, thermally powered, mechanically powered, and electromechanically powered.

18. The catheter system of claim 15 wherein the energy guide is configured to be manually moved by an operator of the catheter system so that the guide distal end of the energy guide moves adjacent to and between the proximal region and the distal region of the treatment site while the energy guide receives energy from the energy source.

19. The catheter system of claim 15 wherein the guide shaft includes a guide channel that guides movement of the energy guide relative to the guide shaft.

20. The catheter system of claim 19 wherein the guide channel has a somewhat spiral configuration along a length of the guide shaft; and wherein the guide distal end of the energy guide moves in a substantially spiral manner while the guide distal end moves adjacent to and between the proximal region and the distal region of the treatment site.

21. The catheter system of claim 19 wherein the guide channel has a somewhat sinusoidal configuration along a length of the guide shaft; and wherein the guide distal end of the energy guide moves in a substantially sinusoidal manner while the guide distal end moves adjacent to and between the proximal region and the distal region of the treatment site.

22. A catheter system for treating a treatment site within or adjacent to a blood vessel within a body of a patient, the treatment site having a proximal region and a distal region, the catheter system comprising:
   an energy source that generates energy, the energy source being configured to generate a plasma, causing rapid bubble formation that imparts pressure waves upon the treatment site;
   a guide shaft that is positionable adjacent to the treatment site, the guide shaft including a guidewire lumen that encircles a guidewire;
   a catheter shaft that is configured to be selectively positioned near the treatment site, the guide shaft being positioned at least partially within the catheter shaft;
   an inflatable balloon that is coupled to the catheter shaft, the inflatable balloon including a balloon wall that defines a balloon interior, the inflatable balloon being configured to retain a balloon fluid within the balloon interior;
   an energy guide that receives energy from the energy source, the energy guide being movably coupled to the guide shaft, the energy guide including a guide distal end that is configured to be positioned within the balloon interior and adjacent to the treatment site, the guide distal end of the energy guide being selectively movable relative to the balloon and the guide shaft and adjacent to and between the proximal region and the distal region of the treatment site while the energy guide receives energy from the energy source, the energy guide guiding the energy from the energy source so that the plasma generation is initiated in the balloon fluid within the balloon interior, the guide distal end of the energy guide being in fluid communication with the balloon fluid in which the plasma is generated; and
   an energy guide mover that selectively moves the energy guide so that the guide distal end of the energy guide moves adjacent to and between the proximal region and the distal region of the treatment site while the energy guide receives energy from the energy source, the energy guide mover including a plurality of motorized rollers that engage the energy guide, the motorized rollers selectively moving the energy guide adjacent to and between the proximal region and the distal region of the treatment site while the energy guide receives energy from the energy source.

23. The catheter system of claim 22 wherein the energy guide mover is one of hydraulically powered, pneumatically powered, electrically powered, magnetically powered, thermally powered, mechanically powered, and electromechanically powered.

24. The catheter system of claim 22 wherein the guide shaft includes a guide channel that guides movement of the energy guide relative to the guide shaft.

25. The catheter system of claim 24 wherein the guide channel has a somewhat spiral configuration along a length of the guide shaft; and wherein the guide distal end of the energy guide moves in a substantially spiral manner while the guide distal end moves adjacent to and between the proximal region and the distal region of the treatment site.

26. The catheter system of claim 24 wherein the guide channel has a somewhat sinusoidal configuration along a length of the guide shaft; and wherein the guide distal end of the energy guide moves in a substantially sinusoidal manner while the guide distal end moves adjacent to and between the proximal region and the distal region of the treatment site.

* * * * *